United States Patent
Dyer et al.

(10) Patent No.: US 8,143,571 B1
(45) Date of Patent: Mar. 27, 2012

(54) METHOD FOR FRACTIONING PEPTIDES AND OTHER COMPOUNDS

(75) Inventors: Daniel J. Dyer, Murphysboro, IL (US); Gary R. Kinsel, Carbondale, IL (US)

(73) Assignee: Southern Illinois University, Carbondale, IL (US)

( * ) Notice: Subject to any disclaimer, the term of this patent is extended or adjusted under 35 U.S.C. 154(b) by 230 days.

(21) Appl. No.: 12/477,753

(22) Filed: Jun. 3, 2009

Related U.S. Application Data

(60) Provisional application No. 61/058,442, filed on Jun. 3, 2008.

(51) Int. Cl.
*C08F 2/36* (2006.01)
*C08F 4/42* (2006.01)

(52) U.S. Cl. ........ 250/281; 250/282; 250/288; 525/310; 525/315; 526/324

(58) Field of Classification Search ............... 250/281, 250/282, 288; 525/310, 315; 526/324
See application file for complete search history.

(56) References Cited

U.S. PATENT DOCUMENTS

| | | | |
|---|---|---|---|
| 6,716,948 B1 * | 4/2004 | Klaerner et al. | 526/303.1 |
| 7,019,082 B2 * | 3/2006 | Matyjaszewski et al. | 525/268 |
| 7,259,217 B2 * | 8/2007 | Klaerner et al. | 526/303.1 |

FOREIGN PATENT DOCUMENTS
EP  1 035 218 A1  9/2000

OTHER PUBLICATIONS

Advincula et al., "Polymer brushes by living anionic surface initiated polymerization on flat silicon and gold surfaces: homopolymers and block copolymers" *Langmuir*, 18:8672-8684 (2002).

Angiolini et al., "Chiroptical switching based on photoinduced proton transfer between homopolymers bearing side-chain spiropyran and azopyridine moieties," *Macromol. Chem. Phys.*, 209(19): 2049-2060 (2008).

Anikin et al., Polyelectrolyte-Mediated Protein Adsorption: Fluorescent Protein Binding to Individual Polyelectrolyte Nanosphere,: *J. Phys. Chem. B.*, 109:5418-5420 (2005).

Asai et al., "Interaction Between an Acidic Extractant and an Octadecylamino Group Introduced into a Grafted Polymer Chain," *Sep. Sci. Technol.*, 40:3349-3364 (2005).

Bai et al., "Peptide Mapping by CNBr Degradation on a Nitrocellulose Membrane with Analysis by Matrix-Assisted Laser Desorption/Ionization Mass Spectrometry," *Anal. Chem.*, 67:1705-1710 (1995).

Bain et al., "Formation of Monolayer Films by the Spontaneous Assembly of Organic Thiols from Solution onto Gold," *J. Am. Chem. Soc.*, 111:321-335 (1989).

Bakhtiar et al., "Electrospray Ionization and Matrix-Assisted Laser Desorption Ionization Mass Spectrometry," *Biochem. Pharmacol.*, 59:891-905 (2000).

(Continued)

*Primary Examiner* — Nikita Wells
(74) *Attorney, Agent, or Firm* — Marshall, Gerstein & Borun LLP

(57) ABSTRACT

A method for fractionating a target fraction from a sample is disclosed herein. The method includes providing a polymer brush having a substrate and a polymer chain attached to and extending outwardly from the substrate. The method further comprising contacting the polymer brush with the sample to allow for sorption of the target fraction by the polymer chain. The polymer chain is then stimulated with a stimulus to contract and release the target fraction.

22 Claims, 7 Drawing Sheets

OTHER PUBLICATIONS

Balamurugan et al., "Thermal Response of Poly(N-isopropylacrylamide) Brushes Probed by Surface Plasmon Resonance," *Langmuir*, 19:2545-2549 (2003).
Bell et al., "Photophysical effects between spirobenzopyran-methyl methacrylate-functionalized colloidal particles," *Langmuir*, 22(4):1420-1427 (2006).
Blackledge et al., "Polyethylene Membrane as a Sample Support for Direct Matrix-Assisted Laser Desorption/Ionization Mass Spectrometric Analysis of High Mass Proteins," *Anal. Chem.*, 67:843-848 (1995).
Blais et al., "MALDI-TOFMS Identification of 'Odorant Binding Proteins' (OBPs) Electroblotted onto Poly(vinylidene difluoride) Membranes," *Rapid Commun. Mass Spectrom.*, 10:1-4 (1996).
Brittain et al. "A Structural Definition of Polymer Brushes," *J. Polym. Sci., Part A: Polym. Chem.*, 45:3505-3512 (2007).
Brockman et al., "Optimization of a Hydrophobic Solid-Phase Extraction Interface for Matrix-Assisted Laser Desorption/Ionization,". *J. Mass Spectrom.*, 3:1141-1147 (1998).
Brockman et al., "New Immobilization Chemistry or Probe Affinity Mass Spectrometry," *Rapid Commun. Mass Spec.*, 10:1688-1692 (1996).
Brockman et al., "Probe-Immobilized Affinity Chromatography/Mass Spectrometry," *Anal. Chem.*, 67:4581-4585 (1995).
Choi et al., "Surface-Initiated Polymerization of I-Lactide: Coating of Solid Substrates with a Biodegradable Polymer", *Macromolecules*, 34:5361-5363 (2001).
de Vos et al., "Adsorption of the Protein Bovine Serum Albumin in a Planar Poly(acrylic acid) Brush Layer as Measured by Optical Reflectometry," *Langmuir*, 24(13):6575-6584 (2008).
Dvornikov et al., "Spectroscopy and Kinetics of a Molecular Memory with Nondestructive Readout for Use in 2D and 3D Storage Systems," *J. Phys. Chem. B.*, 108:8652-8658 2004.
Dyer, "Photoinitiated Synthesis of Grafted Polymers," *Adv. Polym. Sci.*, 97:47-65 2006).
Dyer et al., "Patterning of Gold Substrates by Surface-initiated Polymerization," *Adv. Funct. Mater.*, 13:667-670 (2003).
Edmondson et al., "Polymer Brushes via Surface-Initiated Polymerizaitons," *Chem. Soc. Rev.*, 33:14-22 (2004).
Foerch et al., "Soft Plasma Treated Surfaces: Tailoring of Structure and Properties for Biomaterial Applications," *Plasma Proc. Polym.*, 2:351-372 (2005).
Gorg et al., "The current state of two-dimensional electrophoresis with immobilized pH gradients," *Electroshoresis*, 21(6):1037-1053 (2000).
Gu et al., "Anchoring of Liquid Crystals on Surface-Initiated Polymeric Brushes," *Chem Phys Chem*, 448-451 (2002).
Heegaard, "Applications of affinity interactions in capillary electrophoresis," *Electrophoresis*, 24(22-23):3879-3891 (2003).
Hollmann et al., "Characterization of a Planar Poly(acrylic acid) Brush as a Materials Coating for Controlled Protein Immobilization," *Langmuir*, 22:3300-3305 (2006).
http://www.harricksci.com/accessories/H VariGATR.cfm.
Huang et al., "Controlled Synthesis of Cross-Linked Ultrathin Polymer Films by Using Surface-Initiated Atom Transfer Radical Polymerization," *Angew. Chem. Int. Ed.*, 40:1510-1512 (2001).
Hurst et al., "Analysis for TNF-α Using Solid-Phase Affinity Capture with Radiolabel and MALDI-MS Detection," *Anal. Chem.*, 71:4727-4733 (1999).
Husemann et al. "Surface-Initiated Polymerization for Amplification of Self-Assembled Monolayers Patterned by Microcontact Printing", *Angew. Chem. Int. Ed.*, 38:647-649 (1999).
Hutchens et al., "New Desorption Strategies for the Mass Spectrometric Analysis of Macromolecules," *Rapid Commun. Mass Spectrom.*, 7:576-580 (1993).
Issaq et al., "The SELDI-TOF MS Approach to Proteomics: Protein Profiling and Biomarker Identification," *Biochem. Biophys. Res. Commun.*, 292:587-592 (2002).
Ista et al., "Synthesis of Poly(N-isopropylacrylamide) on Initiator-Modified Self-Assembled Monolayers," *Langmuir*, 17:2552-2555 (2001).

Johnson et al., "Construction of linear polymers, dendrimers, networks, and other polymeric architectures by copper-catalyzed azide-alkyne cycloaddition "click" chemistry," *Macromol. Rapid Commun.*, 29(12-13):1052-1072 (2008).
Jones et al., "Surface-Initiated Polymerizations in Aqueous Media: Effect of Initiator Density," *Langmuir*, 18:1265-1269 (2002).
Jones et al., "Variable Adhesion of Micropatterned Thermoresponsive Polymer Brushes: AFM Investigations of Poly(N-isopropylacrylamide) Brushes Prepared by Surface-Inititiated Polymerizations," *Adv. Mater.*, 14:1130-1134 (2002).
Jordan et al., "Nanocomposites by surface initiated living cationic polymerizatin of 2-oxazolines on functionalized gold nanoparticles" *Macromolecules*, 34:1606-1611 (2001).
Jordan et al., "Surface initiated living cationic polymerization of 2-oxazolines" *J. Am. Chem. Soc.*, 120:243-247 (1998).
Jordan et al., "Surface-Initiated anionic polymerization of styrene by means of self-assembled monolayers" *J. Am. Chem. Soc.*, 121:1016-1022 (1999).
Kaholek et al., "Weak Polyelectrolyte Brush Arrays Fabricated by Combining Electron-Beam Lithography with Surface-Initiated Photopolymerization," *Chem. Mater.*, 18:3660-3664 (2006).
Kawai et al., "Extension and Shrinkage of Polymer Brush Grafted onto Porous Membrane Induced by Protein Binding," *Macromolecules*, 33:1306-1309 (2000).
Kiehntopf et al., "Use of SELDI-TOF Mass Spectrometry for Identification of New Biomarkers: Potential and Limitations," *Clin. Chem. Lab. Med.*, 45:1435-1449 (2007).
Kilar, "Recent applications of capillary soelectric focusing," *Electrophoresis*, 24(22-23):3908-3916 (2003).
Kim et al., "Surface-Initiated Atom Transfer Radical Polymerization on Gold at Ambient Temperature," *J. Am. Chem. Soc.*, 122:7616-7617 (2000).
Kim et al., "Synthesis of Triblock Copolymer Brushes by Surface-Initiated Atom Transfer Radical polymerization," *Macromolecules*, 35:5410-5416 (2002).
Kobatake et al. "Photochromism," *Annu. Rep. Prog. Chem., Sect. C*, 99:277-313 (2003).
Kratzmuller et al., "Ultrathin Microstructured Polypeptide Layers by Surface-initiated Polymerization on Microprinted Surfaces," *Adv. Mater.*, 11:555-558 (1999).
Laschewsky et al., "Reactive Hydrogels Grafted on Gold Surfaces", *Macromol. Symp.*, 164:323-340 (2001).
Laschewsky et al., "Tailoring of Stimuli-Responsive Water Soluble Acrylamide and Methacrylamide Polymers," *Macromol. Chem. Phys.*, 202:276-286 (2001).
Le et al., "Fluorescence polarization detection for affinity capillary electrophoresis," *Electrophoresis*, 23(6):903-908 (2002).
Leermakers et al., "On the Mechanism of Uptake of Globular Proteins by Polyelectrolyte Brushes: A Two-Gradient Self-Consistent Field Analysis," *Langmuir*, 23:3937-3946 (2007).
Li et al., "Synthesis of Well-Defined Polymer Brushes Grafted onto Silica Nanoparticles via Surface Reversible Addition-Fragmentation Chain Transfer Polymerization," *Macromolecules*, 38(14):5929-5936 (2005).
Li et al., "Radio Frequency Plasma Polymer Coatings or Affinity Capture Maldi Mass Spectrometry," *Anal. Chem.*, 77:350-353 (2005).
Li et al., "Thermoresponsive MALDI Probe Surfaces as a Tool for Protein On-Probe Purification," *Anal. Chem.*, 79:6840-6844 (2007).
Liu et al., "Viologen-Functionalized Conductive Surfaces: Physicochemical and Electrochemical characteristics and Stability," *Langmuir*, 18:9041-9047 (2002).
Love et al., "Self-Assembled Monolayers of thiolates on Metals as a Form of Nantechnology," *Chem. Rev.*, 105:1103-1170 (2005).
Maeda et al., "Change in Hydration State During the Coil-Globule Transition of Aqueous Solutions of Poly(N-isopropylacrylamide) as Evidenced by FTIR Spectroscopy," *Langmuir*, 16:7503-7509 (2000).
Merchant et al., "Recent Advancements in Surface-Enhanced Laser Desorption/Ionization-Time of Flight-Mass Spectrometry," *Electrophoresis*, 21:1164-1167 (2000).
Milner, "Polymer Brushes," *Science*, 251:905-914 (1991).
Möller et al., "Stannous(II) Trifluoromethane Sulfonate: A Versatile Catalyst for the Controlled Ring-Opening Polymerization of Lactides: Formation of Stereoregular Surfaces from Polylactide Brushes," *J. Polym. Sci.; Part A: Polym. Chem.*, 39:3529-3538 (2001).
Montgomery et al., "DIABLA: A New Screening Method for the Discovery of Protein Targets," *J. Proteome Res.*, 7(10):4594-4597 (2008).
Montgomery et al., "Dynamic Isoelectric Focusing for Proteomics," *Anal. Chem.*, 78(18):6511-6518 (2006).
Niwa et al., "In Situ Photopolymerization of Methacrylic acid at a self-assembled xanthate monolayer surface on gold. Formation of polymethacrylic acid brushes and their interaction with cytochrome c" *Macromolecules*, 29:3681-3685 (1996).
Osborne et al., "Controlled growth of triblock polyelectrolyte brushes," *Chem. Commun.*, 1838-1839 (2002).
Papac et al., "Direct Analysis of Affinity-Bound Analytes by MALDI/TOF MS," *Anal. Chem.*, 66:2609-2613 (1994).
Paweletz et al., "Rapid Protein Display Profiling of Cancer Progression Directly from Human Tissue using a Protein Biochip," *Drug. Dev. Res.*, 49:34-42 (2000).
Peng et al., "Preparation of Polymer-Silicon(100) Hybrids via Interface-Initiated Reversible Addition-Fragmentation Chain-Transfer (RAFT) Polymerization," *Macromolecules*, 39(16):5577-5582 (2006).
Peng et al., "Reactive-electrospray-assisted laser desorption/ionization for characterization of peptides and proteins," *Anal. Chem.*, 80:6995-7003 (2008).
Petricoin et al., "Proteomic Analysis at the Bedside: Early Detection of Cancer," *Trends in Biotech.*, 20:S30-S34 (2002).
Piech et al., "Controlled synthesis of photochromic polymer brushes by atom transfer radical polymerization," *Macromolecules*, 39(3):915-922 (2006).
Pieper et al., "Multi-component immunoaffinity subtraction chromatography: An innovative step towards a comprehensive survey of the human plasma proteome," *Proteomics*, 3(4):422-432 (2003).
Pirri et al., "Microarray Glass Slides Coated with Block Copolymer Brushes Obtained by Reversible Addition Chain-Transfer Polymerization," *Analytical Chemistry*, 78(9):3118-3124 (2006).
Plunkett et al., "Light-Regulated Electrostatic Interactions in Colloidal Suspensions," *J. Am. Chem. Soc.*, 127:14574-14575 (2005).
Pyun et al., "Synthesis of Polymer Brushes Using Atom Transfer Radical Polymerization," *Macromol. Rapid Commun.*, 24:1043-1059 (2003).
Qian et al., Direct Analysis of the Products of Sequential Cleavages of Peptides and Proteins Affinity-Bound to Immobilized Metal Ion Beads by Matrix-Assisted Laser Desorption/Ionization Mass Spectrometry, *Anal. Biochem.*, 274:174-180 (1999).
Rinsch et al., Pulsed Radio Frequency Plasma Plymerization of Allyl Alcohol: Controlled Deposition of Surface Hydroxyl Groups, *Langmuir*, 12:2995-3002 (1996).
Rosario et al., "Solvatochromic Study of the Microenvironment of Surface-Bound Spiropyrans," *Langmuir*,19:8801-8806 (2O03).
Sabatani et al., "Thioaromatic Monolayers on Gold: A New Family of Self-Assembling Monolayers," *Langmuir*, 9:2974-2981 (1993).
Samanta et al., "Formation of Photochromic Spiropyran Polymer Brushes via Surface-Initiated, Ring-Opening Metathesis Polymerization: Reversible Photocontrol of Wetting Behavior and Solvent Dependent Morphology Changes," *Langmuir*, 24(17):9558-9565 (2008).
Satoh et al., "Selective and sensitive determination of lipoyllysine (protein-bound-a-lipoic acid) in biological specimens by high performance liquid chromatography with fluorescence detection," *Anal. Chim. Acta.*, 618:210-217 (2008).
Schmidt et al., "Photoinitiated Polymerization of Styrene from Self-Assembled Monolayers on Gold," *Langmuir*, 18:1281-1287 (2002).
Schriemer et al., "Combining Avidin-Biotin Chemistry with Matrix-Assisted Laser Desoption/Ionization Mass Spectrometry," *Anal. Chem.*, 68:3382-3387 (1996).
Schriemer et al., "MALDI Mass Spectrometry Combined with Avidin-Biotin Chemistry for Analysis of Protein Modifications," *Anal. Chem.*, 70:1569-1575 (1998).
Senaratne et al., "Self-Assembled Monolayers and Polymer Brushes in Biotechnology: Curnsnt Applications nad Future Perspectives," *Biomacromolecules*, 6:2427-2448 (2005).

Shah et al., "Using Atom Transfer Radical Polymerization to Amplify Monolayers of Initiators Patterned by Microcontact Printing into Polymer Brushes for Pattern Transfer," *Macromolecules*, 33:597-605 (2000).
Shea et al., "Fluorescence probes for evaluating chain solvation in network polymers. An analysis of the solvatochromic shift of the dansyl probe in macroporous styrene-divinylbenzene and styrene-diisopropenylbenzene copolymers," *Macromolecules*, 22(4):1722-30 (1989).
Shimura, "Recent advances in capillary isoelectric focusing: 1997-2001," *Electrophoresis*, 23:3847-3857 (2002).
Stensballe et al., "Simplified Sample Preparation Method for Protein Identification by Matrix-Assisted Laser Desorption/Ionization Mass Spectrometry: in-Gel Digestion on the Probe Surface," *Proteomics*, 1:955-966 (2001).
Tang et al., "Current Developments in SELDI Affinity Technology," *Mass Spectrom. Rev.*, 23:34-44 (2004).
Tang et al., "Matrix-Assisted Laser Desorption/Ionization Mass Spectrometry of Immobilized Duplex DNA Probes," *Nucleic Acids Res.*, 23:3126-3131 (1995).
Tang, "Construction of functional polymers from acetylenic triple-bond building blocks," *Macromol. Chem. Phys.*, 209(13):1303-1307 (2008).
Tomasulo et al., "Bichromophoric photochromes based on the opening and closing of a single oxazine ring," *J. Org. Chem.*, 73(1):118-126 (2008).
Tomasulo et al., "Synthesis and properties of benzophenone-spiropyran and naphthalene-spiropyran conjugates," *J. Org. Chem.*, 72(2):595-605 (2007).
Unlu et al., "Difference gel electrophoresis: A single gel method for detecting changes in protein extracts," *Electrophoresis*, 18(11):2071-2077 (1997).
Walker et al., "Studies of Peptide Binding to Allyl Amine and Vinyl Acetic Acid-Modified Polymers Using Matrix-Assisted Laser Desorption/Ionization Mass Spectrometry," *Anal. Biochem.*, 271:123-130 (1999).
Wan et al., "Fluorescence Polarization Studies of Affinity Interactions in Capillary Electrophoresis," *Analytical Chemistry*, 71(19):4183-4189 (1999).
Wan et al., "Studies of Protein-DNA Interactions by Capillary Electrophoresis/Laser-Induced Fluorescence Polarization," *Analytical Chemistry*, 72(22):5583-5589 (2000).
Wang et al., "A General Method for Producing Bioaffinity MALDI Probes," *Anal. Chem.*, 71:2014-2020 (1999).
Warren et al., "On-Probe Solid-Phase Extraction/MALDI-MS Using lon-Pairing Interactions for the Cleanup of Peptides and Proteins," *Anal. Chem.*, 70:3757-3761 (1998).
Whelan et al., "Affinity assays using fluorescence anisotropy with capillary electrophoresis separation," *Analytical Chemistry*, 76(24)7380-7386 (2004).
Whittle et al., "Adsorption of Vitronectin, Collagen and Immunoglobulin-G to Plasma Polymer Surfaces by Enzyme Linked Immunosorbent Assay (ELISA)," *J. Mater. Chem.*, 2:2726-2732 2002 (2002).
Wittemann et al., "Interaction of Proteins with Linear Polyelectrolytes and Spherical Polyelectrolyte Brushes in Aqueous Solution," *Phys. Chem. Chem. Phys.*, 8:5269-5275 (2006).
Wong et al., "Separation of Peptides with Polyionic Nanosponges for MALDI-MS Analysis," *Langmuir*, 25:1459-1465 (2009).
Xia et al. "Dual-Responsive Surfaces that Switch Between Superhydrophilicity and Superhydrophobicity," *Adv. Mater.*, 18:432-436 (2006).
Xu et al. "Constructing polymer brushes on multiwalled carbon nanotubes by in situ reversible addition fragmentation chain transfer polymerization," *Polymer*, 47(16): 5909-5918 (2006).
Ye et al., "Synthesis, Preparation, and Conformation of Stimulus-Responsive End-Grafted Poly(methacrylic acid-g-ethylene glycol) Layers," *Soft Matter*, 2:243-256 (2006).
Zhang et al., Solid-Phase Extraction/MALDI-MS: Extended Ion-Pairing Surfaces for the On-Target Cleanup of Protein Samples, *Anal. Chem.*, 71:4753-4757 (1999).
Zhao et al., "Principles of Surface-Directed Liquid Flow in Microfluidic Channels," *Anal. Chem.*, 74:4259-4268 (2002).

Zhao et al., "Surface-Directed Liquid Flow Inside Microchannels," *Science*, 291:1023-1026 (2001).
Zhao et al., "Protein Epitope Mapping by Mass Spectrometry," *Anal. Chem.*, 66:3723-3726 (1994).
Zhou et al., "Surface Grafted Polymer Brushes as Ideal Building Blocks for "Smart" Surfaces," *Phys. Chem. Chem. Phys.*, 8:3815-3823 (2006).
Zhu et al., "Spiropyran-Based Photochroic Polymer Nanoparticles with Optically Switchable Luninescence," *J. Am. Chem. Soc.*, 128:4303-4309 (2006).
Ahram et al., "Proteomic Analysis of Human Prostate Cancer," *Mol. Carcinogenesis*, 33:9-15 (2002).
Andreasson et al., "Molecular and Logic Gate Based on Electric Dichroism of a Photochromic Dihydroindolizine," *Angew. Chem. Int. Ed.*, 44:7591-7594 (2005).
Bernards et al., "Nonfouling Polymer Brushes via Surface-Initiated, Two-Component Atom Transfer Radical Polymerization," *Macromolecules*, 41:4216-4219 (2008).
Berhane et al., "Functional Microfabricated Sample Targets for Matrix-Assisted Laser Desorption/Ionization Mass Spectrometry Analysis of Ribonucleic Acids," *Anal. Chem.*, 75:1997-2003 (2003).
Biesheuvel et al., "Self-Consistent Field Theory of Protein Adsorption in a Non-Gaussian Polyelectrolyte Brush," *Phys. Rev. E.*, 73:011802 (2006).
Brockman et al., "A Desalting Approach for MALDI-MS Using On-Probe Hydrophobic Self-Assembled Monolayers," *Anal. Chem.*, 69:4761-4720 (1997).
Bundy et al., "Lectin and Carbohydrate Affinity Capture Surfaces for Mass Sepctrometric Analysis of Microorganisms," *Anal. Chem.*, 73:751-757 (2001).
Clarke et al., "The Application of Clinical Proteomics to Cancer and Other Diseases," *Clin. Chem. Lab. Med.*, 41:1562-1570 (2003).
Feng, "Synthesis and Characterization of Functional Organic Thin Films by Surface Initiated Polymerizations," Ph. D. Dissertation, Southern Illinois University, 2005.
Friedrich et al., "Polymer Surface Modification with Monofunctional Groups of Variable Types and Densities," *J. Adhesion Sci. Technol.*, 17:1591-1617 (2003).
Hobbs et al., "Synthesis of Polymerized Thin Films for Immobilized Ligand Display in Proteomic Analysis," *Bioconj. Chem.*, 14:526-531 (2003).
Hyun et al., "Surface-Initiated Free Radical Polymerization of Polystyrene Micropatterns on a Self-Assembled Monolayer of Gold," *Macromolecules*, 34:5644-5652 (2001).
Ingall et al., "Surface Functionalization with Polymer and Block Copolymer Films Using Organometallic Initiators," *J. Am. Chem. Soc.*, 122:7845-7846 (2000).
Ito, "Chemical Amplification Resists for Microlithography" *Adv. Polym. Sci.*, 172:37-245 (2005).
Li et al., "Well-controlled polymerization of 2-azidoethyl methacrylate at near room temperature and click functionalization," *J. Polym. Sci., Part A: Polym. Chem.*, 45(18):4300-4308 (2007).
Liang et al., "Synthesis and Properties of Photochromic Fluorescing 2-Indolyl Fulgide and Fulgimide Copolymers," *Macromolecules*, 35:9377-9382 (2002).
Liang et al., "On-Probe Immunoaffinity Extraction by Matrix-Assisted Laser Desorption/Ionization Mass Spectrometry," *Anal. Chem.*, 70:498-503 (1998).
Minko, "Responsive Polymer Brushes," *Macromol. Sci., Part C: Polym. Rev.*, 46:397-420 (2006).
Neubert et al., "Enhanced Affinity Capture MALDI-TOF MS: Orientation of an Immunoglobulin G Using Recombinant Protein G," *Anal. Chem.*, 74:3677-3683 (2002).
Reichmanis et al., "A Novel Approach to O-Nitrobenzyl Photochemistry for Resists," *J. Vac. Sci. Technol.*, 19(4)1338-42 (1981).
Ren et al., "Solvent polarity scale on the fluorescence spectra of a dansyl monomer copolymerizable in aqueous media," *Chem. Phys. Lett.*, 307(1,2):55-61 (1999).
Seibert et al., "Surface-Enhanced Laser Desorption Ionization Time-of-Flight Mass Spectrometry (SELDI TOF-MS) and ProteinChip® Technology in Proteomics Research," *Pathol., Res. Pract.*, 200:83-94 (2004).
Siuzdak et al., "Applications of Mass Spectrometry in Combinatorial Chemistry," *Biotechnol. Bioeng.*, 61:127-134 (1998).
Tomasulo et al., "Fast and Stable Photochromic Oxazines," *J. Org. Chem.*, 70:8180-8189 (2005).
Wan et al., "Capillary electrophoresis coupled with laser-induced fluorescence polarization as a hybrid approach to ultrasensitive immunoassays," *Journal of Chromatography A*, 853(12):555-562 (1999).
Wan et al., "Capillary electrophoretic immunoassays for digoxin and gentamicin with laser-induced fluorescence polarization detection," *Journal of Chromatography B: Biomedical Sciences and Applications*, 734(1):31-38 (1999).
Wang et al. "Photon Gated Transport at the Glass Nanopore Electrode," *J. Am. Chem. Soc.*, 128:13553-13558 (2006).
Wang et al., "Detection of Serum Proteomic Changes and Discovery of Serum Biomarkers for Kashin-Beck Disease using Surface-Enhanced Laser Desorption Ionization Mass Spectrometry (SELDI_TOF MS)," *J. Bone Miner. Metab.*, 26:385-393 (2008).
Weston et al., "Systems Biology, Proteomics, and the Future of Health Care: Toward Predictive, Preventative, and Personalized Medicine," *J. Proteome Res.*, 3:179-196 (2004).
Xiong et al., "Use of a lectin affinity selector in the search for unusual glycosylation in proteomics," *J. Chrom. B*, 782(1-2):405-418.
Xu et al., "Patterned Monolayer/Polymer Films for Analysis of Dilute or Salt-Contaminated Protein Samples by MALDI-MS," *Anal. Chem.*, 75:185-190 (2003).
Xu et al., "Determination of Enantiomeric Composition by Fluorescence Anisotropy," *J. Phys. Chem. A*, 108:6929-6932 (2004).
Xu et al., "Fluorescence Anisotropy as a Method to Examine the Thermodynamics of Enantioselectivity," *J. Phys. Chem. B*, 109:8144-8152 (2005).
Yang et al., "Capillary Electrophoresis and Fluorescence Anisotropy for Quantitative Analysis of Peptide-Protein Interactions Using JAK2 and SH2-Bb as a Model System," *Analytical Chemistry*, 77(8):2482-2489 (2005).
Zhang et al., "Modeling of Living Free Radical Polymerization with Raft Chemistry," *Ind. Eng. Chem. Res.*, 40:4336-4352 (2001).
Zhang et al., "Surface Modification by Continuous Graft Copolymerization. I. Photoinitiated Graft Copolymerization onto Polyethylene Tape Film Surface," *J. Appl. Polym. Sci.*, 40:1647-1661 (1990).
Limbach et al., Spectroscopy, 13:16-27 (1998).
Advincula et al., (Eds.), Polymer Brushes: Synthesis, Characterization, Applications. 2004, Wiley-VCH, Weinheim, pp. 1-483.
Ballauff et al., "Polyelectrolyte Brushes," *Curr. Opin. Colloid Interface Sci.*, 11:316-323 (2006).
Buckingham et al., "Evaluation of amino acid based polymer brushes for use as chiral stationary phases," Abstracts of Papers, 231st ACS National Meeting, Atlanta, GA, United States, Mar. 26-30, 2006, ANYL-228 (unpublished results).
Bulman, "Strategies for Discovery and Characterization of Protein Biomarkers by SELDI-TOF MS," *Am. Biotechnol. Lab.*, 26(2):14-16 (2008).
Chiefari et al.. "Control of Free-Radical Polymerization by Chain Transfer Methods", Handbook of Radical Polymerization. Edited by Krzysztof Matyjaszewski and Thomas P. Davis. John Wiley & Sons, Inc.: Hoboken, p. 629-690 (2002).
Constable et al., "Characterization of polymer brushes in capillaries," *Colloids Surf.*, A, 308(1-3):123-128 (2007).
Czeslik, "Factors Ruling Protein Adsorption," *Z. Phys. Chem.*, 218:771-801 (2004).
Denes et al., "Macromolecular Plasma-Chemistry: An Emerging Field of Polymer Science," *Prog. Polym. Sci.*, 29(8):815-885 (2004). Abstract Only.
Dyer et al., "Synthesis, Characterization, Application," *Polymer Brushes, Eds.*, Chp. 1, p. 129-150, Wiley-VCH (2004).
Futami et al., "Conformations of nitro-substituted spiropyran and merocyanine studied by lowtemperature matrix-isolation IR spectroscopy and density-functional-theory calculation," *Chem. Phys. Lett.*, 370:460-468 (2003).
Goias et al., "Click chemistry and ATRP: a beneficial union for the preparation of functional materials," *Qsar Comb. Sci.*, 26 (11-12):1116-1134 (2007).

Gopireddy et al., "Room Temperature Growth of Surface-Confined Poly(acrylamide) from Self-Assembled Monolayers Using Atom Transfer Radical Polymerization," *Macromolecules*, 35:4218-4221 (2002).

Griesser et al., "Surface-MALDI Mass Spectrometry in Biomaterials Research," *Biomaterials*, 25:4861-4875 (2004).

Hawker et al., "Bringing efficiency to materials synthesis: The philosophy of click chemistry," *Aust. J. Chem.*, 60(6):381-383 (2007).

Hodgetts et al., "Biomarker Discovery in Infectious Diseases Using SELDI," *Fut. Microbiol.*, 2:35-49 (2007).

Jackson et al., "Mass Spectrometry for Genotyping: An Emerging Tool for Molecular Medicine," *Mol. Med. Today*, 6:271-276 (2000). Abstract Only.

Kim et al., "Enzymatic surface initiated polymerization of 3-(R)-hydroxybutyrl-coenzyme A: Surface modification of a solid substrate with a biodegradable and biocompatible polymer: Poly(3-hydroxybutyrate)," *Polymer Preprints*, 43(1):706-707 (2002).

Kowalski et al., "Accelerating Discoveries in the Proteome and Genome with MALDI TOF MS," *Pharmacogenomics*, 1:359-366 (2000).

Krongauz, "Photochromic Polymers," *Mol. Cryst. Liq. Cryst.*, 246:339-346 (1994).

Le Droumaguet et al., "Click chemistry: a powerful tool to create polymer-based macromolecular chimeras," *Macromol. Rapid Commun.*, 29(12-13):1073-1089 (2008).

Lukyanov et al., "Spiropyrans: Synthesis, Properties, and Application", *Chem. Heter. Compds.*, 41:281-311 (2005).

Lutz et al., "Modern trends in polymer bio-conjugates design," *Prog. Polym. Sci.*, 33(1):1-39 (2008).

Mauri et al., "Fractionation Techniques Improve the Proteomic Analysis of Human Serum," *Curr. Pharm. Anal.*, 4:69-77 (2008).

Mori et al., "Design of novel polymeric architectures with (meth)acrylic acid segments by controlled/living polymerizations," Living and Controlled Polymerization: Synthesis, Characterization and Properties of the Respective Polymers and Copolymers, 257-288 (2006). Table of Contents Only.

Nagasaki et al., "An Intelligent Polymer Brush," *Trends Polym. Sci.*, 4:59-64 (1996).

Niwa, "Biomarker Discovery for Kidney Diseases by Mass Spectrometry," *J. Chromato gr., B: Anal. Technol. Biomed. Life Sci.*, 870:148-153 (2008).

Oehr, "Plasma Surface Modification of Polymers for Biomedical Use," *Nuc. Instrum. Meth. Phys. Res., Sec. B*, 208:40-47 (2003).

Park et al., "Identification of Proteomic Biomarkers of Preeclampsia in Amniotic Fluid Using SELDI-TOF Mass Spectrometry," *Reproductive Sciences*, 5(5):457-468 (2008).

Paweletz et al., "Proteomic Patterns of Nipple Aspirate Fluids Obtained by SELDI-TOF: Potential for New Biomarkers to Aid in the Diagnosis of Breast Cancer," *Disease Markers*, 17:301-307 (2001).

Poncin-Epaillard et al., "Surface Engineering of Biomaterial with Plasma Techniques," *J. Biomat. Sci., Polym. Ed.*, 14:1005-1028 (2003).

Roecken et al., "Proteomics in Pathology, Research and Practice," *Pathol. Res. Pract.*, 200:69-82 (2004).

Rühe et al., "Functional Polymer Brushes," *J. Macromol. Sci.: Polym. Rev.*, C42:91-138 (2002).

Rühe et al., "Polyelectrolyte Brushes," *Adv. Polym. Sci.*, 165:79-150 (2004).

Sankhe et al., "Polymerization of Poly(Itaconic Acid) on Surfaces by Atom Transfer Radical Polymerization in Aqueous Solutions," *Mat. Res. Soc. Symp. Proc.*, 710:277-282 (2002).

Shen et al., "PEO-Like Plasma Polymerized Tetraglyme Surface Interaction with Leukocytes and Proteins: *in vitro* and *in vito* Studies," *J. Biomat. Sci., Polym. Ed*, 13(4):367-390 (2002).

Sun et al., "Structure Analysis of Poly(N-isopropylacrylamid) Using Near-Infrared Spectroscopy and Generalized Two-Dimensional Correlation Infrared Spectroscopy," *Appl. Spectrosc.*, 61:765-771 (2007).

Thissen et al., "Two-Dimensional Patterning of Thin Coatings for the Control of Tissue Outgrowth," *Biomaterials*, 27(1):35-43 (2006). Abstract Only.

Travaille et al., "Highly Oriented Self-Assembled Monolayers as Templates for Epitaxial Calcite Growth," *J. Am. Chem. Soc.*, 125:11571-11577 (2003).

Tseng et al., "Identification and Structural Elucidation of Lectin-Binding Oligosaccharides by Bioaffinity Matrix-Assisted Laser Desorption/Ionization Fourier Transform Mass Spectrometry," *Analytical Chemistry*, 73(15):3556-3561 (2001).

Weck et al., "Ring-Opening Metathesis Polymerization from Surfaces" *J. Am. Chem. Soc.*, 121:4088-4089 (1999).

Weinberger et al., Spectral Techniques in Proteomics; CRC/Taylor & Francis: London, pp. 101-132 (2007).

Wittemann et al., "Controlled Release of Proteins Bound to Spherical Polyelectrolyte Brushes," *Z Phys. Chem.*, 221:113-126 (2007).

Worrall et al., "Purification of Contaminated Peptides and Proteins on Synthetic Membrane Surfaces for Matrix-Assisted Laser Desorption/Ionization Mass Spectrometry," *Anal. Chem.*, 70:750-756 (1998).

Wu et al., "Non-Fouling Surfaces Produced by Gas Phase Pulsed Plasma Polymerization of an Ultra Low Molecular Weight Ethylene Oxide Containing Monomer," *Colloids surf. B: Biointerfaces*, 18:235-248 (2000).

Xu et al., "Use of Polymer-Modified MALDI-MS Probes to Improve Analyses of Protein Digests and DNA," *Anal. Chem.*, 76:3106-3111 (2004).

Yan et al., "Application of DNA microarray technology in genetics," *Current Topics in Human Genetics*, 375-396 (2007).

Zhang et al., "Modification of gold surface by grafting of poly(ethylene glycol) for reduction in protein adsorption and platelet adhesion," *J. Biomater. Sci. Polym. Ed.*, 12:515-531 (2001).

Zhao et al., "Polymer Brushes: Surface-Immobilized Macromolecules," *Prog. Polym. Sci.*, 25:677-710 (2000).

Lomas et al., Handbook of Biosensors and Biochips; Wiley & Sons Ltd.: Chichester, pp. 885- 894 (2007).

McCarroll et al., Principles of Molecular Absorption and Luminescence, in Encyclopedia of Analytical Chemistry, R. Meyers, Editor. 2000, Wiley: New York. p. 10259-10305.

Seki, "Photomechanical Responses in Photochromic Molecular Films and Related Polymers" in Handbook of Photochemistry and Photobiology, vol. 2: Organic Photochemistry, Nalwa, H.S., Ed.; American Scientific Publishers, Chp. 9, 435-465 (2003.

* cited by examiner

METHOD FOR FRACTIONING PEPTIDES AND OTHER COMPOUNDS

CROSS REFERENCE TO RELATED APPLICATION

The benefit under 35 U.S.C. §119(e) of U.S. Provisional Patent Application No. 61/058,442 filed Jun. 3, 2008, the disclosure of which is incorporated herein by reference, is hereby claimed.

STATEMENT OF GOVERNMENTAL INTEREST

This invention was made with government support under grant nos. CHE-0719426, EEC-021059, and CHE-0094195 awarded by the National Science Foundation, and grant no. NIGMS-R15GM083325 awarded by the National Institutes for Health. The government has certain rights in the invention.

BACKGROUND OF THE INVENTION

1. Field of the Disclosure

The disclosure relates to a method of fractionating a mixed sample to obtain a target fraction. More particularly, the disclosure relates to a method of fractionating a target fraction with a polymer brush that selectively sorbs the target fraction on contact, and contracts in response to a stimulus to release the target fraction.

2. Background Description of Related Technology

Matrix assisted laser desorption ionization mass spectrometry (MALDI MS) is a powerful mass spectrometry technique that allows for the characterization of a variety of biomolecules. MALDI MS however suffers considerable loss of performance in the direct characterization of complex peptide/protein mixtures. In response to this limitation, isolation of the peptide/protein of interest is typically performed prior to MALDI MS.

Traditional peptide/protein isolation/purification methods include liquid chromatography and one-dimensional or two-dimensional polyacrylamide gel electrophoresis. These techniques, while effective for isolation and purification of peptides and proteins, are laborious and time consuming, and thus are not compatible with high-throughput characterization techniques, including MALDI MS. Other fractionation techniques such as on-MALDI-target and off-MALDI-target techniques suffer from a variety of problems, including limitations in the capacity to bind the peptide/protein of interest to separate it from a mixture, and inefficiencies in releasing the peptide/protein of interest for subsequent MALDI MS analysis.

SUMMARY OF THE INVENTION

One aspect of the invention includes a method including providing a polymer brush that includes a substrate and a polymer chain attached to and extending outwardly from the substrate; contacting the polymer brush with a sample including a mixture of a target fraction and a non-target fraction; sorbing the target fraction with the polymer chain; and, releasing the target fraction from the polymer chain by stimulating the polymer chain with a stimulus to contract the polymer chain.

In one embodiment of the invention, the method includes fractionating first and second target fractions from a sample that includes a mixture of the first and second target fractions by contacting the sample to a polymer brush comprising a substrate and a polymer chain attached to and extending outwardly from the substrate, selectively sorbing one of the first and second fractions from the sample with the polymer chain, and releasing the sorbed fraction from the polymer chain by stimulating the polymer chain with a first stimulus to contract the polymer chain.

In one embodiment of the invention, the method includes fractionating first and second target fractions from a sample comprising a mixture of the first and second target fractions by providing a polymer brush having a substrate and polymer chain attached to and outwardly extending from the substrate; contacting the polymer brush with the sample including first and second target fractions; selectively sorbing the first target fraction with the polymer chain, wherein the second target fraction remains on a surface of the polymer brush; removing the second target from the surface of the polymer brush; and, stimulating the polymer chain with a stimulus to contract the polymer chain and release the sorbed first target fraction.

Another aspect of the invention includes a method of assaying for a target fraction in a sample by providing a polymer brush having a substrate and a polymer chain attached to and extending outwardly from the substrate; contacting the polymer brush with a sample; selectively sorbing a target fraction from the sample, if present; stimulating the polymer chain with a stimulus to contract the polymer chain and release the sorbed fraction, if present; and, characterizing the released fraction to detect the presence of the target fraction. In one embodiment, the assay is for a target compound, and a target fraction, potentially containing the target compound, is selectively sorbed, and then the released fraction is characterized to detect the presence of the target compound.

In one embodiment of the invention, the method of assaying for a target fraction in a sample includes contacting a sample to a polymer brush having a substrate and a polymer chain attached to and extending from the substrate; selectively sorbing a target fraction, if present, with the polymer chain, and stimulating the polymer chain with a first stimulus to contract the polymer chain and release the sorbed target fraction, if present.

In one embodiment of the invention, a kit for performing a method of fractionating a target fraction includes a polymer brush and instructions for performing a method described herein.

Another aspect of the invention includes a method of extracting a target fraction from a sample containing first and second fractions by contacting the sample to a polymer brush array having a substrate with first and second polymer brushes, selectively sorbing the first fraction with the first polymer brush and the second fraction with the second polymer brush, and selectively stimulating the first polymer brush to contract and release the first fraction. The polymer brushes each include a polymer chain attached to and outwardly extending from the substrate.

Another aspect of the invention includes an array of polymer brushes that includes a substrate, a first polymer brush comprising a first polymer chain attached to the substrate, and a second polymer brush comprising a second polymer chain attached to the substrate. The first polymer chain selectively sorbs a first fraction and the second polymer chain selectively sorbs a second fraction. The first polymer chain contracts in response to a first contracting stimulus to release a sorbed first fraction, and the second polymer chain contracts in response to a second contracting stimulus to release a sorbed second fraction.

For the compositions, apparatus, and methods described herein, preferred features, such as components, compositional ranges thereof, substituents, conditions, and steps, can be selected from the various embodiments and examples described herein.

Further aspects and advantages will be apparent to those of ordinary skill in the art from a review of the following detailed description, taken in conjunction with the drawings. While the inventive compositions, apparatus, and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIG. 4a is a MALDI spectrum characterizing a mixture of the peptides buccalin and bradykinin using a conventional MALDI target as illustrated in the schematic of FIG. 4a. FIGS. 4b and 4c are MALDI spectra characterizing the peptides buccalin and bradykinin after fractionation using a method in accordance with an embodiment of the invention, as illustrated in the schematics of FIGS. 4b and 4c.

DETAILED DESCRIPTION

Figure 1:
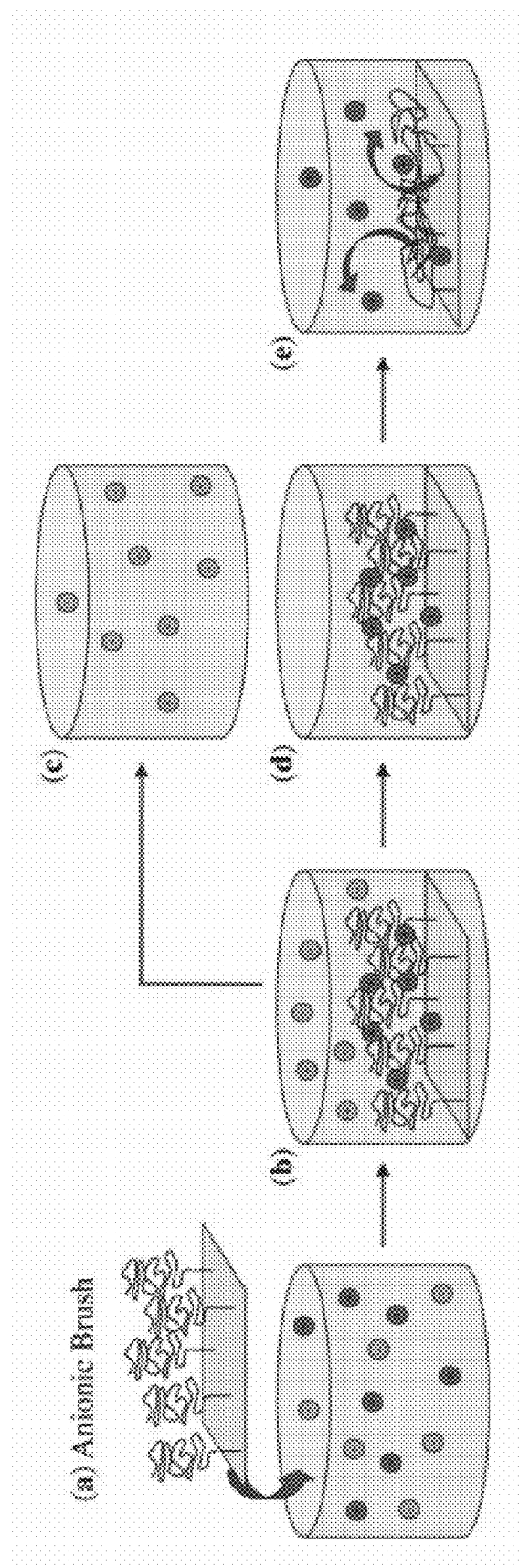
FIG. 1 is a schematic showing a method of fractionating a target fraction in accordance with an embodiment of the invention.

One aspect of the invention disclosed herein is a method of fractionating a target fraction from a sample that includes the target fraction and a non-target fraction. Referring to FIG. 1, the method includes providing a polymer brush that is responsive to a stimulus. The polymer brush includes a substrate and a polymer chain that is attached to and outwardly extends from the substrate. The polymer chain can reversibly contract in response to a stimulus, and preferably also can reversibly expand in response to a stimulus. The stimulus can include, for example, a change in pH, a change in ionic strength (e.g. salt concentration), application of and/or change in a magnetic field, application of and/or change in an electric field, irradiation, change in temperature, or combinations thereof.

The polymer brush is then contacted with the sample and the target fraction is sorbed by the polymer chain (steps a and b of FIG. 1). For example, a droplet of an aqueous sample can be placed on the polymer brush to allow the polymer chain to sorb the target fraction. The polymer chain preferably selectively sorbs only the target fraction from the sample. For example, the polymer chain can be cationic and can selectively sorb an anionic target fraction from a sample comprising the anionic target fraction and a cationic non-target fraction. Alternatively, for example, the polymer chain can be anionic and sorb a cationic target fraction from a sample comprising a cationic target fraction and an anionic non-target fraction.

The polymer chain can also be a neutral (nonionic) species that selectively sorbs ionic target fractions, or the polymer chain can be a neutral species that becomes ionic in response to a stimulus, for example, absorption of electromagnetic radiation. The polymer chain can be a neutral species that selectively sorbs a target fraction through chemical and/or physical interactions. In one embodiment a neutral polymer chain selectively sorbs a target fraction through a hydrophobic interaction. In another embodiment, a neutral polymer chain selectively sorbs a target fraction through a hydrophilic interaction. In yet another embodiment, a neutral polymer chain selectively sorbs a target fraction using hydrogen bonding. In another embodiment, a neutral polymer chain selectively sorbs a target fraction through pi-stacking interaction. In yet another embodiment, a neutral polymer chain selectively sorbs a target fraction through coordination group interactions. In another embodiment, a neutral polymer chain selectively sorbs a target fraction by chelation. In one embodiment the polymer chain has a predominately negative charge (anionic) at a pH of less than 7, for example, 6.22. The predominately negative charge (anionic) polymer chain can selectively sorb a predominately positive charge (cationic) target fraction. In any of the embodiments described herein, sorption of the target fraction is contemplated to include absorption and/or adsorption of the target fraction. In one preferred class, the sorption is by absorption. In another preferred class, the sorption is by adsorption. In still another preferred class, the sorption is by both absorption and adsorption.

The polymer brush and related methods are contemplated to include embodiments including any combination of one or more of the additional optional elements, features, and steps further described below (including those shown in the figures), unless stated otherwise.

In preferred embodiments, the polymer brush will rapidly sorb the target fraction. In one embodiment, the method includes contacting the sample with the polymer brush (e.g., leaving the sample on the polymer brush) for about 10 minutes or less. In other embodiments, the contact time can be less than 10 minutes, 7 minutes or less, 5 minutes or less, or 3 minutes or less, for example. For example, the sample can be left on the polymer brush for a time in a range of 1 second to 10 minutes, 5 seconds to 8 minutes, 10 seconds to 5 minutes, and 30 seconds to 2 minutes. In general, increasing the amount of time the sample is left on the polymer brush will increase the relative amount of target fraction sorbed from the sample. In preferred embodiments, substantially all of the target fraction will be sorbed by the polymer chain in 5 minutes or less, more preferably 2 minutes or less, and even more preferably 1 minute or less.

In another embodiment, the method further includes stimulating the polymer chain with a stimulus to expand the polymer chain. The polymer chain can be stimulated to expand, for example, prior to contacting the polymer chain with the sample. Alternatively, the sample can provide the stimulus. The polymer chain can be contacted with the sample having the stimulus and stimulated to expand substantially simultaneously. For example, the non-target fraction of the sample can include a pH buffer solution. By contacting this sample with a polymer brush having a polymer chain that expands in response to a change in pH, the polymer chain can be triggered to expand while in contact with the sample and sorbing the target fraction. In one embodiment, sorption of the target fraction by a polymer brush is enhanced when the polymer chain is expanded. For example, in one specific embodiment, it is contemplated that absorption of the target fraction by the polymer chain is enhanced when the polymer chain is expanded.

The method can further include selectively removing a non-target fraction of the sample if it remains on the polymer brush after sorption of the target fraction (steps c and d of FIG. 1) and removal of the polymer brush from contact with the sample. Any suitable method for removal of a material from a polymer surface can be used. For example, the non-target fraction of the sample can be dried and then washed away from the polymer brush using a wash that does not stimulate the polymer chain to expand or contract. Alternatively, the non-target fraction can be removed, for example, using a pipette.

The target fraction can be released from the polymer chain, preferably after at least substantial removal of the non-target fraction, by stimulating the polymer chain with a stimulus that causes the polymer chain to contract (step e of FIG. 1). Contraction of the polymer chain facilitates removal of the maximum amount of target fraction sorbed on and/or in the polymer chain.

In one aspect, the method includes selectively sorbing the non-target fraction of the sample with the polymer chain. The target fraction remains unsorbed on the polymer brush and can be removed using any suitable method. For example, the target fraction can be washed from the polymer brush, preferably using washing mixtures that do not stimulate the polymer chain to contract and release the non-target fraction.

In another embodiment, a sample containing a mixture of first and second target fractions are fractionated by selectively sorbing the first target fraction with the polymer chain by contacting the polymer brush with the sample. For example, the first target fraction can be cationic and the second target fraction can be anionic. Furthermore, the polymer brush can include a polymer chain that selectively sorbs cationic species. The polymer brush can be contacted with the sample to allow the polymer chain to selectively sorb the first target fraction. The second target fraction can be removed from the polymer brush after the first target fraction is sorbed by the polymer chain. The polymer chain can then be stimulated with a stimulus the causes the polymer chain to contract and release the first target. In another embodiment, the method of separating the first and second target fractions includes stimulating the polymer chain with a stimulus to expand the polymer chain prior to sorbing the first target fraction. Preferably, the expansion will increase the polymer chain's extent of sorption (e.g., capacity and/or sorption strength).

In another aspect, an array of polymer brushes can be used to fractionate a sample. Each of the polymer brushes and/or groups of polymer brushes in the array can be designed, for example, to selectively sorb a single target fraction from a sample. The polymer brushes in the array can be designed to selectively sorb one or more fractions of a sample. For example, a polymer brush array having three polymer brushes can be used to fractionate first, second, and third target fractions from a sample, with each of the brushes having different sorption characteristics that allow it selectively sorb one of the target fractions. Any suitable number of polymer brushes can be included in the array to selectively sorb any number of target fractions from a sample. Sorption of the target fraction by the polymer brushes and extraction of the target fraction from the polymer brushes can be performed as described above. The polymer brushes in the array can also be designed to react to the same stimulus to substantially simultaneously expand to sorb the target fraction or fractions and/or contract to release the sorbed target fraction or fractions. Alternatively, the polymer brushes in the array can be designed to react to different stimuli, which can allow for selective stimulation of the polymer brushes to sorb and/or release the target fractions.

The methods of the invention can further include characterization of the target fraction or the non-target fraction using, for example, MALDI MS, or other analytical methods including, but not limited to, fluorescence spectroscopy, surface plasmon spectroscopy, and secondary ion mass spectrometry.

The above-described fractionation methods can also be used for detection of a target fraction in a sample. The detection method preferably includes providing a polymer brush that includes a substrate and a polymer chain attached to and outwardly extending from the substrate; contacting the polymer brush with the sample to allow for selective sorption of the target fraction, if present; stimulating the polymer chain with a stimulus to contract the polymer chain and release the sorbed fraction, if present. The method can further include characterizing the released fraction. The released fraction can be characterized, for example, using MALDI MS. The above-described polymer brush array can be used, for example, to detect one or more target fractions in a sample.

The method of the invention can be used to fractionate a variety of target fractions. The target fraction can include biomolecules, including, but not limited to, oligonucleotides, antigens, antibodies, polymers, polypeptides, and polysaccharides. In addition or in the alternative, the target fraction can include other organic molecules, including, but not limited to polymers, dendrimers, hyperbranched polymers, catenanes, and rotaxanes. The target fraction can be an ionic species. For example, the target fraction can include anionic peptides, or, in another embodiment, cationic peptides. Furthermore, the target fraction can also be a neutral species.

The polymer brushes may be able to sorb more of a target fraction as compared self-assembled monolayers possessing similar functional groups as the polymer chain of the polymer brush. For example, a densely packed self-assembled monolayer of mercaptohexadecanoic acid on gold contains about 4.5 molecules/nm$^2$, and a 10×10 nm$^2$ substrate contains a maximum of 450 carboxylate binding sites. A self-assembled monolayer having a thickness of about 2.1 nm yields about 2 carboxylates/nm$^3$. In contrast, a densely packed polymer brush of poly(acrylic acid) could have about 2500 carboxylate binding sites, or about 12 carboxylates/nm$^3$ for the same volume. Accordingly, a 10×10×10 nm$^3$ volume would have about 12,000 carboxylates.

The polymer brush can also be used to selectively extract a fraction or component of a sample. For example, a polymer brush or an array of polymer brushes can be used to fractionate a sample and selectively extract a component from the sample. The polymer brush array can include polymer brushes disposed along a length of a substrate. Each polymer brush and/or groups of polymer brushes can be provided with functionalities capable of sorbing a specific component from the sample. This can allow for spatial separation of components of a sample along a substrate. For example, a sample having first and second components can be fractionated by contacting the sample to a polymer brush array having first and second polymer brushes. The first and second polymer brushes selectively sorb the first and second components, respectively. Once the components are selectively sorbed by the first and second polymer brushes, one of the polymer brushes can be selectively stimulated to contract and release the sorbed fraction. For example, the first polymer brush can be selectively stimulated with a first stimulus to release the first fraction. The second fraction remains sorbed on the second, non-stimulated polymer brush, thereby allowing for the selective extraction of the first fraction. Optionally, the second polymer brush can be selectively stimulated with a second stimulus (same or different from the first type of stimulus) to contract and release the second fraction after removal of the first fraction. Any number of polymer brushes can be used to fractionate a sample having any number of components and to selectively extract any one or more of the components.

Any of the above described methods can be performed as fully automated, and optionally massively parallel processes in which a machine, such as a robot, is programmed to add the desired amount of a sample to a polymer brush or brushes and conduct any one or more of the stimulating, washing, and/or removing steps.

Suitable robotic instruments are known for high-throughput screening. For example, the machine can include a microplate containing a plurality of individual wells or regions each including one or polymer brushes described herein. The machine will also include a liquid handling system to deliver liquid to the brush-containing wells or regions, e.g. in amounts in a range of 0.5 to 200 µl, by using a multi-channel pipetting head. For example, a 96-channel pipetting head can be used with a microplate containing 96, 384, or 1586 wells or regions containing brushes. In the alternative, for example, the solution can be contacted to the polymer brushes by inkjet deposition. The machine can include a rail-mounted robotic arm that moves the plate and/or pipetting head. Stimulation of the brushes on the microplate can be performed in the same apparatus or in a separate combined stimulation/collection and reading apparatus.

The Polymer Brush

The polymer brush includes a polymer chain attached to and extending outwardly from a substrate. In one preferred embodiment, the polymer brush includes an array of polymer chains attached to and extending outwardly from the substrate. To allow for sorption of the target fraction, the polymer chain is provided with a functionality that is complementary to the functionality of the target fraction. For example, when the target fraction is anionic, the polymer chain can be provided with a cationic functionality. Similarly, when the target fraction is cationic, the polymer chain can be provided with an anionic functionality. The functionality can be provided inherently in the brush design (e.g., choice of materials), or via an external stimulus.

The polymer brush can be formed using any suitable method, such as those disclosed in Kaholek et al., *Chem. Mater.* 18:3660-3664 (2006), the disclosure of which is incorporated herein by reference. Polymer brushes have been synthesized by a variety of initiating mechanisms including anionic, cationic, ring-opening (ROP), ring-opening metathesis (ROMP), free radical, controlled radical, enzymatic, and organometallic catalysts. Radical polymerizations are preferred for many applications due to a tolerance for moisture, and a wide variety of organic functional groups. These grafting methods are well-known to those skilled in the art and are disclosed in: European Patent No. 1035218; J. Rühe, W. Knoll, *J. Macromol. Sci.: Polym. Rev.,* C42, 91-138 (2002); B. Zhao, W. J. Brittain, *Prog. Polym. Sci.,* 25:677-710 (2000); Y. Nagasaki, K. Kataoka, *Trends Polym. Sci.,* 4:59-64 (1996); S. Edmondson, V. L. Osborne, W. T. S. Huck *Chem. Soc. Rev.,* 33:14-22 (2004); J. Pyun, T. Kowalewski, K. Matyjaszewski *Macromol. Rapid. Commun.,* 24:1043-1059 (2003); S. T. Milner, *Science,* 251:905-914 (1991), the disclosures of which are incorporated herein by reference.

The polymer chain can be attached to the substrate, for example, by a covalent or a non-covalent bond. Photochemical initiated free radical polymerizations are particularly useful since they may be performed under a diverse range of reaction conditions. For instance, photochemical initiated free radical polymerization can be performed at various temperatures and/or with different solvent concentrations; where initiation is controlled by irradiation with ultraviolet light. The polymer chain is preferably attached to the substrate using a grafting-from technique. A grafting-from process utilizes a polymer initiator that is covalently linked to the substrate through a self assembled monolayer (SAM) such that the polymer extends outwardly from the substrate; this process is termed surface initiated polymerization. The photochemical synthesis of grafted polymers by grafting-from techniques has been disclosed by Dyer, D. J.; Feng, J.; Fivelson, C.; Paul, R.; Schmidt, R.; Zhao, T. In *Polymer Brushes*; Advincula, R. C., Brittain, W., Caster, K., Rühe, J., Eds., Chp. 7, p. 129 (Wiley-VCH: New York, 2004), the disclosure of which is disclosed herein by reference. A particular advantage to photoinitiation from self-assembled monolayers is the ability to pattern substrates as disclosed in Dyer, D. J. *Adv. Funct. Mater.,* 13:667-670 (2003), the disclosure of which is incorporated herein by reference. Furthermore, grafting from polymer substrates, such as polyolefins has been described where photosensitizers, such as benzophenone, are used to create free radicals on thin polymer films as disclosed in Zhang, P. Y.; Ranby, B. *J. Appl. Polym. Sci.,* 40:1647-1661 (1990), the disclosure of which is incorporated herein by reference. The polymer chain can also be attached to the substrate using a grafting-to process.

Figure 2:
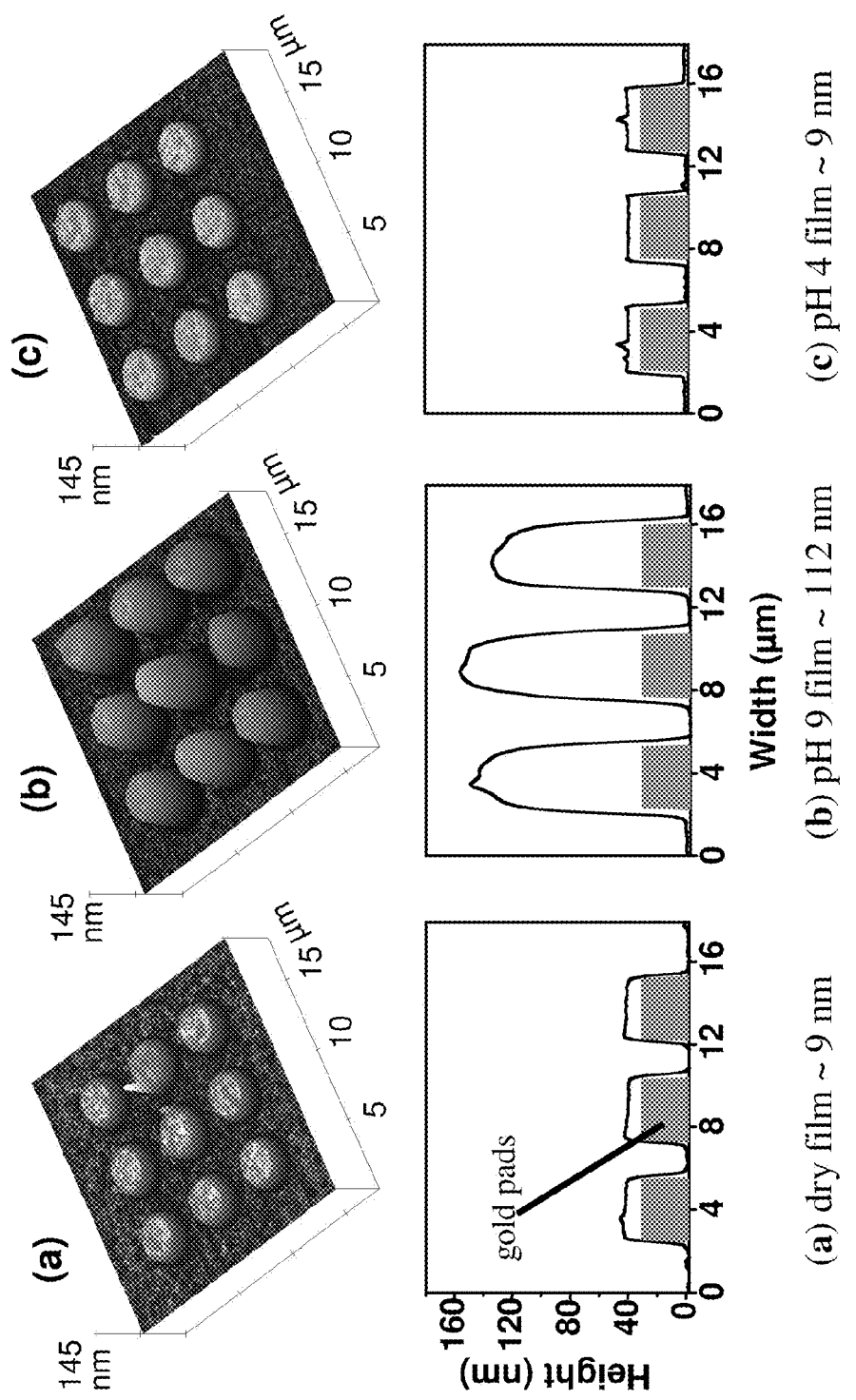
FIG. 2 is atomic force microscopy (AFM) images showing expansion and contraction of polymer chains of a polymer brush.

Referring to FIG. 2, the polymer chain expands and contracts in response to a stimulus. The polymer brush of the embodiment shown in FIG. 2 includes copolymer 1 (see FIG. 3) as its polymer chain. The collapsed polymer brush has a height of 9 nm (in the orientation shown in the figure). Referring to FIG. 2(b), during chain expansion the polymer chain extends away from the substrate increasing the height (in the orientation shown in the figure) of the polymer brush. In the embodiment shown in FIG. 2, the polymer brush expands to a height of 112 nm after contact with a pH 9 buffer solution. Referring to FIG. 2(c), during chain contraction the polymer chain collapses towards the substrate decreasing the height (in the orientation shown in the figure) of the polymer brush. In the embodiment shown in FIG. 2, the polymer brush contracts to its original height upon contact with a pH 4 solution. The polymer chain can, for example, expand to facilitate sorption of the target fraction and/or contract to facilitate release of the target fraction. In one preferred type of embodiment, the stimulus is a change in pH. More preferably, the polymer brush expands in response to an increase in pH and contracts in response to a decrease in pH. Other stimuli can include, for example, application of and/or change in a magnetic field, change in ionic strength (e.g. salt concentration), irradiation, application of and/or change in an electric field, change in temperature, and combinations thereof.

The polymer chain of the polymer brush can include, for example, a homopolymer, a random copolymer, a block copolymer, or a hyperbrached polymer. Preferably, a portion of the monomers making up the polymer chain is of the structure described in Formula 1.

Formula 1:

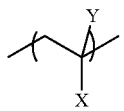

The functional group Y can consist of hydrogen, ($C_1$-$C_{20}$) alkyl, ($CH_2OC_nH_{2n+1}$) alkoxy, ($C_1$-$C_{20}$) fluoroalkyl, ($CH_2OC_nF_{2n+1}$) fluoroalkoxy, aryl, halogen, nitrile, hydroxy or any combination thereof. The functional group Y can also include a carbonyl functionality, for example, an ester or amide. The functional group Y can include an O or S atom forming a portion of an ether functionality. Further, the functional group Y can include a phosphorous atom, for example, in phosphines, phosphine oxides, phosphonate esters, or sulfur containing equivalents.

The functional group X can be, for example, intrinsically ionic. For example, the functional group X can include quaternary ammonium salts, N-alkyl pyridines, nitrogen oxide, and combinations thereof. Alternatively, the functional group X can include functionalities that become ionic at a specific pH. The pH sensitive functionalities can include, for example, hydroxyls, carboxylic acids, pyridines, amines, sulfonic acids, phosphoric acids, and any combination thereof.

In another type of embodiment, the functional group X can be neutral. The neutral functional group can sorb with the target fraction containing, for example crown-ethers, aryl-quadrupoles (e.g. pi-stacking), or hydrogen bonds. The neutral functional group can, for example, form a complex with a molecule, or chelate to an ion. The neutral functional group can also, for example, interact with a target fraction through hydrophobic or hydrophilic interactions.

The functional group X can also be, for example, a neutral functional group that transforms into an ionic species upon absorption of electromagnetic radiation. Alternatively, the functional group X can be an ionic species that transforms into a neutral species upon absorption of electromagnetic radiation. Examples includes, but are not limited to, photoacids and other photoisomerizable functional groups, such as spiropyran, oxazine, fulgimide, dihydroindolizine, o-nitrobenzyl ester, alpha-diazoketone, and diazonium salt.

The functional group X can be, for example, identical to the functional group Y. Alternatively, the functional group X can be, for example, different from the functional group Y.

The polymer brush can include any one or more of a variety of substrates. For example, suitable inorganic substrates can be formed from silver, gold, indium-tin-oxide, magnetic iron oxide, and combinations thereof. Suitable inorganic substrates can be formed from silicon oxide, for example, silicon wafers, glass, mica, quartz, silica gel, silica micro- or nanoparticles, and combinations thereof. Additionally, a suitable substrate can be formed from a combination of inorganic and organic substrates. The substrates can also be formed, for example, from organic polymer films, such as, but not limited to, polystyrene, polyacrylates, polymethacrylates, polyolefins, polyesters, polysiloxanes, polyamides, polycarbonates, and combinations thereof. Conducting polymers such as polythiophenes, polyacetylenes, polysilanes, polyphenylenevinylene, or carbon nanotube composites are also suitable. Substrates formed from conducting polymers can be used, for example, with a polymer chain that is stimulated by an electrical field. Other organic polymer films include biopolymers or members and hyperbranched polymers, such as dendrimers. Other suitable substrates include high surface area oxides, such as alumina, silica, sol-gels (including inorganic based sol-gels, e.g. aluminum silicates, titanium dioxide, zirconium dioxide, metal fluorides, and other oxides); substrates formed from the nucleus of a hyperbranched polymer, such as a dendrimer; Cd/Se nanoparticles, magnetic iron-oxide nanoparticles, or other micro- or nanoparticles; carbon nanotubes; microfluidic channels; capillaries; and membranes. In one preferred embodiment, the polymer brush includes a polymer chain that is attached to a MALDI target to form a polymer brush-modified MALDI target.

A kit for performing a method of fractionating a target fraction from a sample comprising the target fraction and a non-target fraction can be provided and includes the above-described polymer brush and instructions for performing any one of the above-described methods.

The following example is provided for illustration and is not intended to limit the scope of the invention.

EXAMPLE

MALDI Analysis of Non-Fractionated Buccalin and Bradykinin Peptide Mixture

Figure 4:
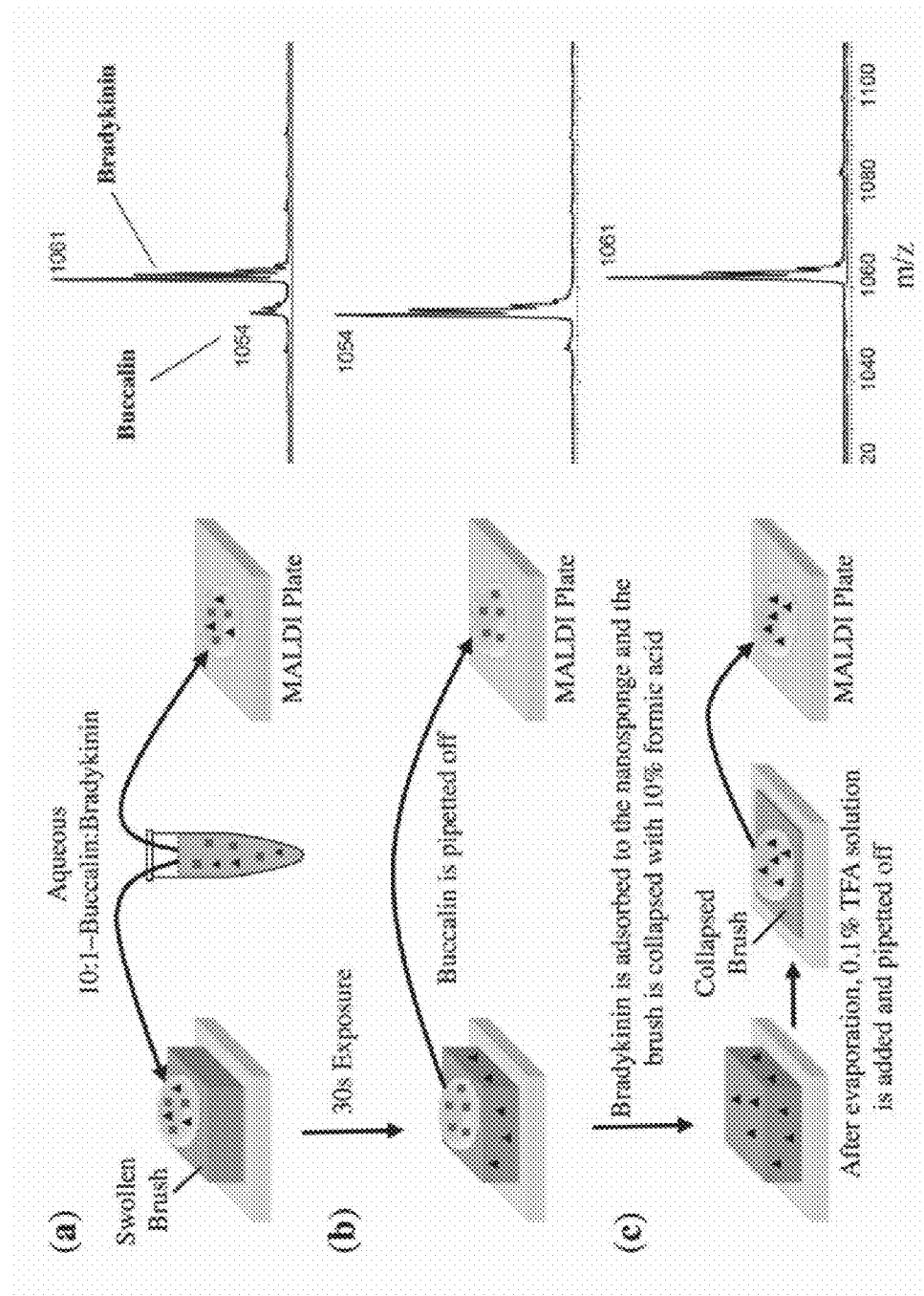

A droplet containing a 10:1 mixture of buccalin and bradykinin (~30 pmol of bradykinin per 7 $mm^2$ droplet) was placed on a gold substrate containing copolymer 1. The substrate was then analyzed using MALDI MS. Referring to FIG. 4a, even with a 10-fold excess of buccalin, the MALDI signal is barely detectable compared to the bradykinin. This is because of the reduced ionization efficiency of buccalin in the presence of the basic bradykinin.

Formation of a MALDI Target Modified with a Polymer Brush

Figure 3:
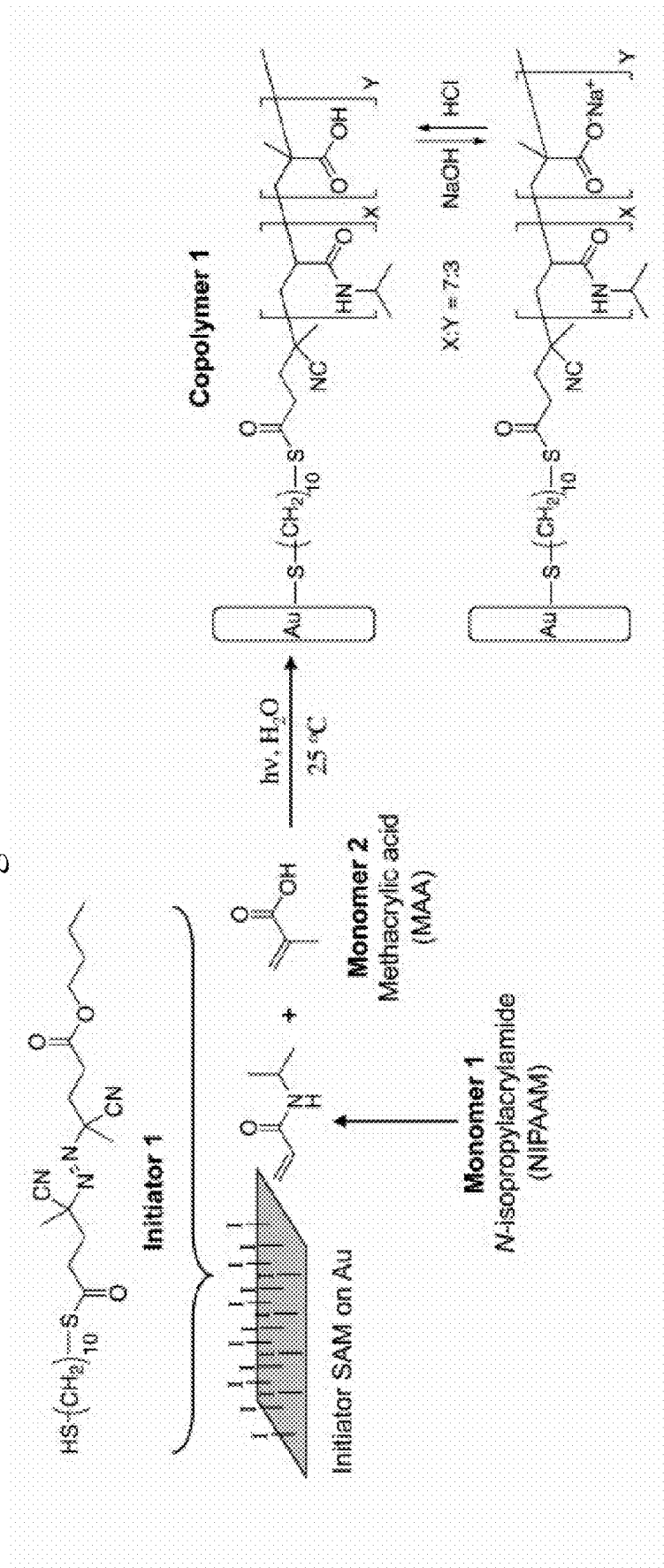
FIG. 3 is a schematic showing the formation of a polymer brush.

Referring to FIG. 3, polymer brushes were formed onto gold-coated silicon wafers substrates. The substrates were chemically cleaned for 120 min in Piranha solution and then rinsed with copious amounts of nanopure water. Next, a self assembled monolayer (SAM) containing initiator 1 was formed by immersing the substrates into a dilute (1 mM) tetrahydrofuran (THF) solution of initiator 1 for at least 12 hours.

The samples were removed from the initiator solution, rinsed thoroughly with THF, and blown dry with liquid-nitrogen boil-off. Deposition of the monolayer of initiator 1 was confirmed by reflection absorption infrared spectroscopy (RAIRS) and water contact angle measurements. RAIS confirmed the presence of MAA with a carbonyl band at 1732 $cm^{-1}$, which indicated hydrogen bonding, most likely with the NIPAAM. The hydrogen bonding dimer, which is normally at about 1690 $cm^{-1}$, partially overlaps with a broad band at 1662 $cm^{-1}$ because of the NIPAAM. The presence of NIPAAM was confirmed with carbonyl and amide bands at 1662 $cm^{-1}$ and 1528 $cm^{-1}$, respectively. Infrared spectra were recorded on a NICOLET-670 FTIR spectrometer equipped with a liquid-nitrogen cooled MCT-B detector and a PIKE grazing angle accessory; all spectra were collected at an 80° grazing angle. The sample chamber was purged with nitrogen gas for 20 minutes prior to data acquisition.

Static contact angles of samples were measured with a CAM 100 (KSV INSTRUMENTS) contact angle meter at room temperature. Contact angles were collected and averaged from the measurements at three different spots on each substrate to yield a water contact angle of 74°.

Polymerization experiments were initiated immediately following initiator SAM deposition. Polymerization was carried out in a RAYONET photochemical reactor (model RMR-600, SOUTHERN NEW ENGLAND ULTRAVIOLET CO., Branford, Conn.). Referring to FIG. 3, the SAM containing initiator 1 coated substrate was placed into a Schlenk tube with a solution containing N-isopropylacrylamide (756 mg) (monomer 1) and methacrylic acid (324 mg) (monomer 2) in water (5 mL) to form a polymer brush having copolymer 1.

The ratio of monomer 1 to monomer 2 in the solution was approximately 7:3. Approximately 30% of the monomer units in the copolymer contained carboxylate functional groups at a basic pH. The Schlenk tube was purged with argon, degassed by three successive freeze-pump-thaw cycles, and was back-filled with argon prior to irradiation at 350 nm (~1.6 mW/cm$^2$). The substrates were removed after a specified irradiation time at room temperature, and were then rinsed with a 1:1 solution of methanol and Millipore-filtered water. The substrate was then immersed into a vial containing the same solution overnight. The substrate was removed and rinsed with fresh solution and then was immersed again for 24 hours. The neutral brush-modified substrate had a static water contact angle of 79°.

Fractionating a Buccalin and Bradykinin Mixture

A 2 µl droplet of Millipore-filtered water was placed onto the polymer brush surface and was allowed to stand for 30 minutes; the average spot diameter was 3 mm. Next, a 1 µl aliquot of a solution containing a mixture of the peptides buccalin and bradykinin was applied onto the spot. Referring to FIG. 4a, the solution was allowed to stand for 30 seconds to allow for absorption of the cationic bradykinin onto the polymer brush. Referring to FIG. 4b, after 30 seconds, the solution remaining on the spot was removed with a pipette and was added onto a conventional MALDI plate surface. Three subsequent 1 µl aliquots of water were added and removed immediately by pipette and were added onto the same spot on the MALDI plate. A matrix solution consisting of 15 mg/ml α-cyano-4-hydroxy cinnamic acid (CHCA) in 0.1% trifluoroacetic acid (TFA) was then added to the conventional MALDI plate. Referring to FIG. 4b, MALDI analysis of the removed solution confirmed that only buccalin was removed.

Referring to FIG. 4c, to remove the bradykinin from the polymer brush, a matrix solution consisting of 15 mg/ml CHCA in 10% formic acid (FA) was added onto the spot and allowed to dry. A solution consisting of the same matrix (15 mg/ml CHCA) in 0.1% Trifluoroacetic acid (TFA) was added to the washings on the conventional MALDI plate. The matrix solution neutralized the carboxylates of the polymer brush, causing the brush to contract and release the absorbed bradykinin. Referring to FIG. 4c, MALDI analysis was performed to determine the concentration of bradykinin recovered from the polymer brush. As illustrated in FIGS. 4a-4c, isolation of the buccalin peptide from the bradykinin improved detection of the buccalin and demonstrated rapid fractionation of the two peptides.

Data acquisition and analysis was performed using a BRUKER MICROFLEX MALDI mass spectrometer with a nitrogen laser at 337 nm. The laser intensity was kept at 33%-35% and 100 laser shots were averaged. The linear mode was used for analysis and all spectra were calibrated using internal standards. The delay time was 150 ns and ions below mass/charge 500 were deflected.

Polymer Brush Sorption Capacity Analysis

To measure the sorption capacity of the polymer brush a 1 µL aliquot of the peptide bradykinin was applied to each of (1) a conventional stainless steel MALDI target, (2) a gold-coated substrate modified with a thin polymer film resulting from RF-plasma polymerization of vinyl-acetic acid, and (3) a gold-coated substrate containing a 30:70 PMAA/PNIPAAM brush polymer. The aliquot was allowed to stand for 30 seconds on each of the MALDI targets. The aliquot remaining on the surface (which contained any unbound bradykinin) of each MALDI target was then removed and deposited on separate conventional stainless steel MALDI targets. MALDI analysis of these MALDI targets was then performed to determine the amount of unbound bradykinin removed from each of the MALDI targets. The signal associated with the unbound bradykinin was recorded by acquiring a MALDI mass spectrum.

The capacity of each target was tested at bradykinin concentrations of 0.01 mg/mL, 0.05 mg/mL, 0.1 mg/mL, 0.5 mg/mL, 1.0 mg/mL, and 2.0 mg/mL. Tables 1 and 2 shows the value of the MALDI signal (in arbitrary units of intensity) resulting from MALDI analysis of the unbound bradykinin collected from each MALDI target. Table 2 represents the average value and standard deviation of additional testing of the sorption capacity of the MALDI targets. The above-described testing procedures were used to obtain the data of Table 2.

TABLE 1

| Original Bradykinin Concentration | Conventional Stainless Steel MALDI Target | MALDI Target Modified by rf Plasma Polymerization | MALDI Target Modified with the Polymer Brush |
|---|---|---|---|
| 2.0 mg/mL | 2959 | 2903 | 870 |
| 1.0 mg/mL | 1982 | 1556 | 877 |
| 0.5 mg/mL | 2953 | 2600 | 453 |
| 0.1 mg/mL | 1774 | 912 | 190 |
| 0.05 mg/mL | 1522 | 1031 | 222 |
| 0.01 mg/mL | 1436 | 765 | 175 |

TABLE 2

| Original Bradykinin Concentration | Conventional Stainless Steel MALDI Target | Gold-Coated Substrate Modified by rf Plasma Polymerization | Gold-Coated Substrate Modified with the Polymer Brush |
|---|---|---|---|
| 2.0 mg/mL | 3136 ± 815 | 2903 ± 1151 | 870 ± 157 |
| 1.0 mg/mL | 1667 ± 656 | 1556 ± 748 | 877 ± 209 |
| 0.5 mg/mL | 1221 ± 280 | 814 ± 257 | 453 ± 107 |
| 0.1 mg/mL | 626 ± 291 | 550 ± 564 | 190 ± 65 |
| 0.05 mg/mL | 852 ± 495 | 623 ± 262 | 222 ± 143 |
| 0.01 mg/mL | 763 ± 302 | 650 ± 238 | 175 ± 28 |

The large standard deviations in Table 2 are typical for MALDI experiments (i.e. relative standard deviations in a range of 25% to 40% are common), which can be the result of and derive from inhomogenous distribution of the MALDI matrix/analyte crystals on the surface of the probe. The results of Tables 1 and 2 illustrate that at the highest bradykinin concentration the signals from the unbound bradykinin from both the conventional stainless steel and rf plasma polymer-modified thin film surfaces are nearly identical and likely represent saturation of the target binding sites. The signal from the unbound bradykinin eluted from the rf plasma polymer surface only becomes measurably lower than the bradykinin eluted from the stainless steel surface at applied bradykinin concentrations at, or below, 0.5 mg/mL. This suggests that at bradykinin concentrations above this value the surface binding sites of the rf plasma polymer thin film are essentially saturated. Notably, however, the signal resulting from the bradykinin from the brush polymer surface was substantially lower than that obtained from either of the other two surfaces.

This result suggests that the capacity of the polymer brush was not exceeded event at bradykinin concentrations of 2.0 mg/mL.

A 1 µL aliquot of 2 mg/ml bradykinin solution contains about $1.1 \times 10^{15}$ molecules of bradykinin. This aliquot interacts with about 3.1 mm² of polymer brush material surface area, leading to a surface concentration of $3.7 \times 10^{14}$ molecules/mm². In contrast, if the cross-sectional area of a bradykinin molecule is about $1.6 \times 10^{-12}$ mm²/molecule, then a monolayer of bradykinin on a microscopically smooth surface, such as a SAM thin film, will have a surface concentration of about $6.2 \times 10^{11}$ molecules/mm². The amount of bradykinin deposited on the brush polymer surface for the highest concentration solution is nearly 600 times the monolayer coverage amount, and still appears to be below the saturation limit of the brush polymer. Without intending to be bound by theory, it is believed that the increased capacity of the polymer brush is related to penetration of the bradykinin into the bulk of the conformationally expanded polymer brush and not just a result of surface adsorption of the bradykinin on a highly roughened surface.

Time Dependence of Absorption of Bradykinin Peptide on the Polymer Brush

Figure 5:
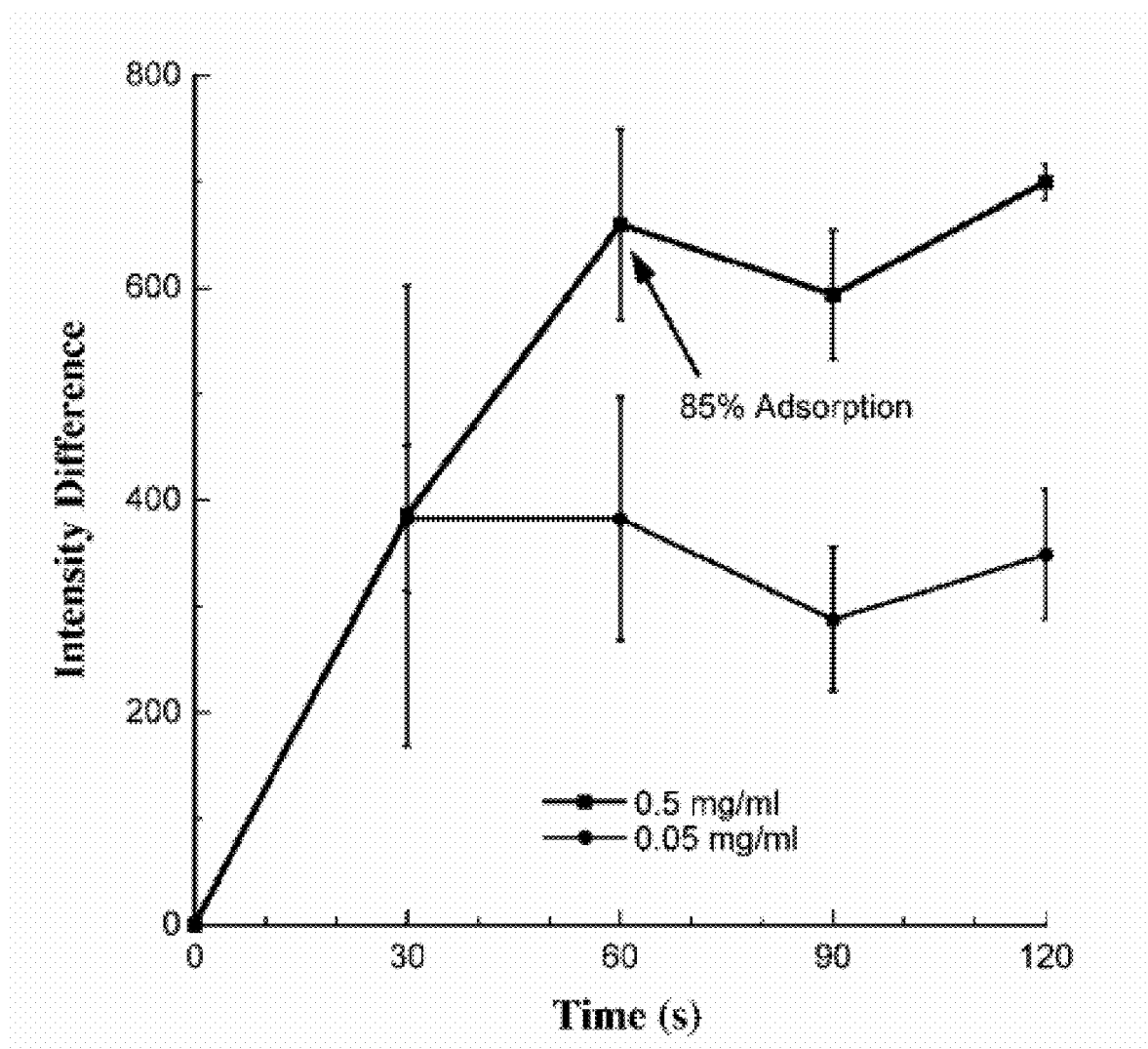
FIG. 5 is a graph showing the uptake of bradykinin from solution at 0.5 and 0.05 mg/ml concentration of bradykinin. The y-axis represents the relatively intensity difference for the MALDI signal between the original solution and the solution removed from the polymer brush at the specified time.

The above-described capacity measurement procedure was used with a MALDI target modified with the polymer brush to test the time dependence of the bradykinin absorption by the polymer brush. The 1 µL aliquot of the peptide bradykinin was allowed to stand on the polymer brush for 30, 60, 90, and 120 seconds. The remaining solution was removed and analyzed with MALDI MS to determine the amount of unbound bradykinin. The time dependence study was performed for varying initial bradykinin concentrations (0.5 mg/mL to 0.05 mg/mL). FIG. 5 represents the uptake of bradykinin as the difference in intensity of the MALDI signal from the initial solution at time 0 and eluant at 30 second intervals, for initial concentrations of 0.5 and 0.05 mg/mL). The intensity of the bradykinin signal decreased 85% after 1 minute for the 0.5 mg/ml sample, suggesting that the majority of adsorption occurred within this time frame. Both concentrations rapidly leveled off, indicating that equilibrium is reached within about 2 minutes. The results show that the uptake of bradykinin continued to increase by approximately 1 order of magnitude over a period of 2 minutes. Accordingly, the amount of unbound bradykinin eluted from the polymer brush continued to decrease by an order of magnitude over a period of 2 minutes. Without intending to be bound by theory, it is believed that this temporal response is most likely a reflection of the time-dependence associated with the reorganization of the polymer brush and penetration of the bradykinin within the bulk of the material. Diffusion rates within the initial 1 µL drop alone cannot explain a 2 minute uptake of bradykinin.

Brush Ellipsometry Studies

A RUDOLPH RESEARCH thin-film null ellipsometer (Model 43603-200E) was used in the brush ellipsometry studies. The polymer brush consisted of a layer of 30% MAA/70% NIPAAM on a gold coated QCM crystal, synthesized in accordance with published procedures. See Kaholek et al., 18 Chem. Mater. 3660-3664 (2006). A pH 1.0 phosphate buffer (S11M03) was used from RADIOMETER. The buffer was diluted 10 times to make the salt concentration less than 10 mM as a stock solution. The pH 7.0 stock solution was then used to make 0.01 mg/ml bradykinin and buccalin solutions. Ellipsometry measurements with different peptide flush sequences were carried out. The polymer sample was immersed in 20 ml of pH 7.0 stock solution overnight to equilibrate the swelling of the polymer brush. Ellipsometry data was first collected in pH 7.0 stock solution. After $\Delta$ and $\Psi$ curves leveled off, the sample cuvette was flushed with buccalin solution (at 500 seconds). After about 20 minutes (at about 1750 seconds), the sample cuvette was flushed and immersed with bradykinin solution. The sample cuvette was then flushed with pH 4.0 stock solution for 5 minutes to protonate the MAA residues in order to release the adsorbed peptides on the polymer brush. Finally, the polymer brush was immersed in pH 7.0 solution for 5 minutes to deprotonate the MAA residues, which rehydrated the collapsed the polymer brush, preparing it for further experiments.

Figure 6:
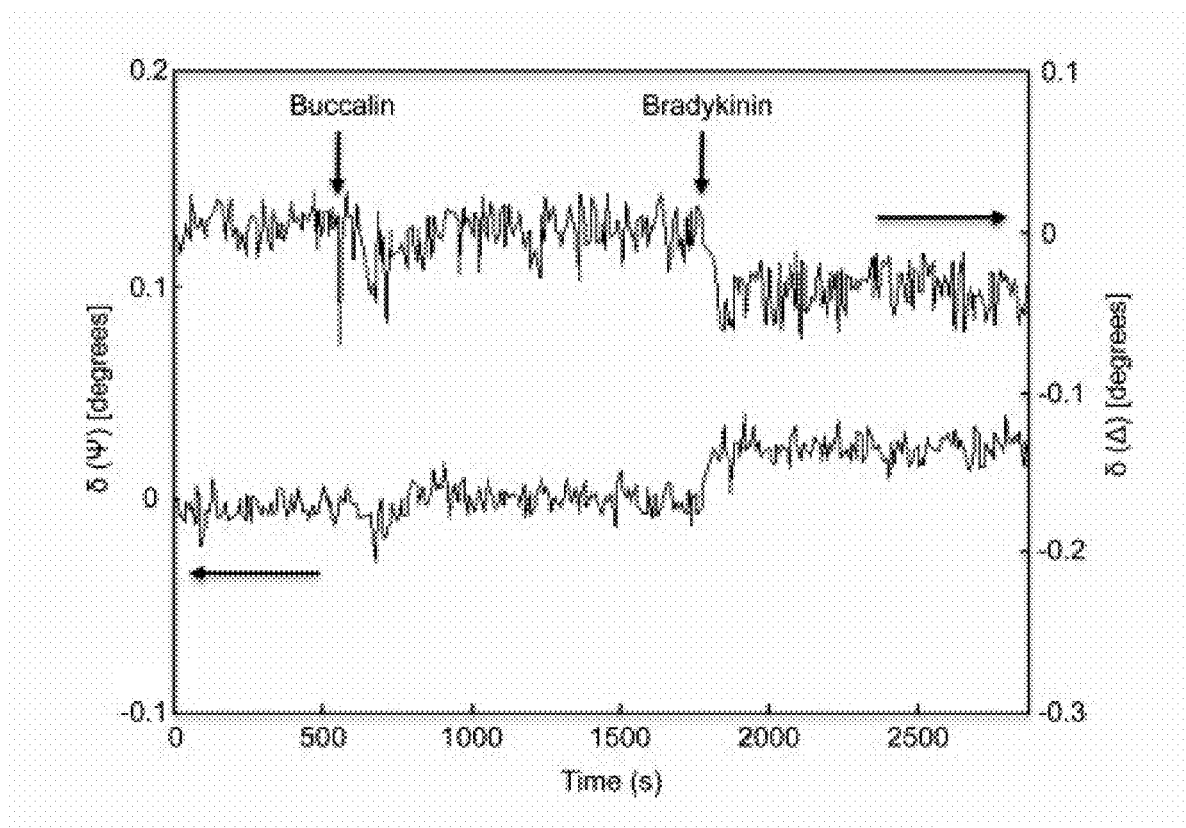
FIG. 6 is a graph showing the adsorption of buccalin and bradykinin on a PNIPAAM/PMAA brush as measured by liquid mode ellipsometry.

Referring to FIG. 6, the addition of buccalin solution at 500 seconds had only a transient effect on brush conformation. The brush returned to its initial state in about 2 minutes. This suggests that buccalin likely did not intercalate or bind to the anionic brush, except perhaps at the brush-solvent interface. In contrast, the addition of bradykinin solution at 1750 seconds caused a rapid and persistent conformational change. This is consistent with the result illustrated in FIG. 6 and further illustrates that the selective uptake of bradykinin begins immediately and is most rapid during the first minute.

Fractionation of Glu C Digest of the BSA Protein

Protein bovine serum albumin (BSA) was digested using a common Glu C enzyme, which cleaves the protein at any glutamic acid residue. Glu C was prepared by dissolving 250 µL of 100 mM $NH_4HCO_3$ buffer. The enzyme solution was separated into 25 µL aliquots and stored at $-20°$ C. Digests were prepared by adding 125 µL of Glu C solution to 100 µL of protein solution. A 5 mg/mL protein solution was prepared in 100 mM $NH_4HCO_3$, pH 8 buffer. The Glu C solution and the protein solution were incubated for 18 hours at 37° C. The solution was then diluted using the 5 mg/ml digest and 50% acetonitrile in water to a concentration of 2 mg/ml.

Figure 7:
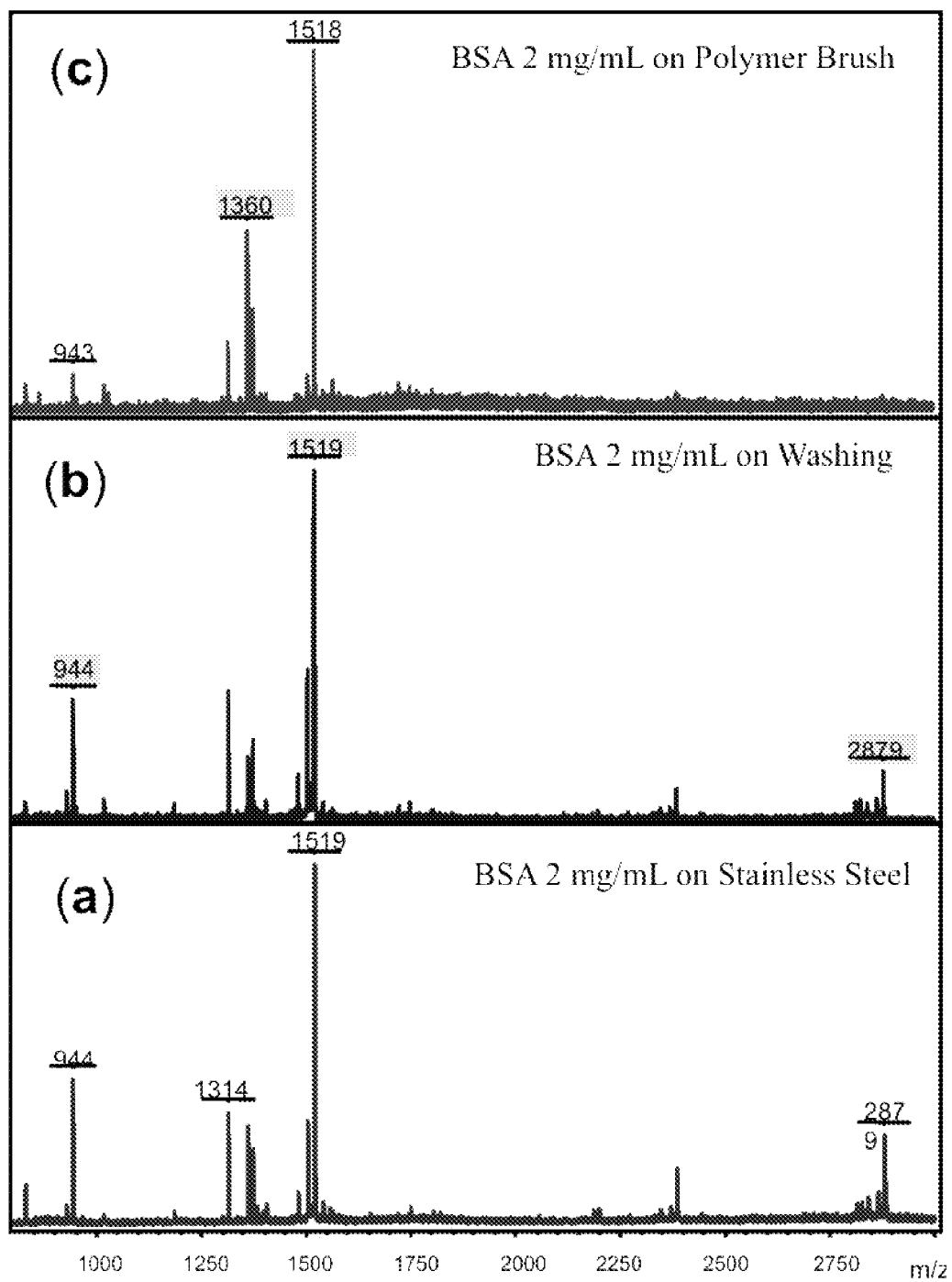
FIG. 7 are MALDI spectrum characterizing (a) a mixture of digested BSA with Glu C enzyme on a stainless steel substrate, (b) the eluant after the mixture was exposed to a polymer brush using a method in accordance with an embodiment of the invention, and (c) the fraction of the mixture sorbed on the polymer brush.

A 1 µL aliquot of the digest solution was applied to a conventional stainless steel MALDI target and a MALDI target containing the polymer brush. The aliquot was allowed to stand for 30 seconds on each of the MALDI targets. The aliquot remaining on the surface of each MALDI target was then removed and deposited on separate conventional stainless steel MALDI targets. MALDI analysis of these MALDI targets was then performed. A MALDI spectrum of the stainless steel MALDI substrate is illustrated in FIG. 7a, and show peaks at 2879, 1519, and 944 mass units, which represents the original solution. As shown in FIG. 7b, these same peaks are present in the eluant after the original solution has been exposed to the polymer brush. FIG. 7c is a MALDI spectrum of the fraction of the solution absorbed by the polymer brush. FIG. 7c shows new peaks that were not present in either the original solution or the eluant. For example, new peaks are exhibited at 1518, 1260, and 943 mass units. Furthermore, the peaks above 1700 mass units, which were present in both the original solution and the brush eluant were no longer detected in the fraction absorbed by the polymer brush. The example illustrates that the invention can detect new protein digest peptides, which can improve the confidence of protein identification through conventional database searching protocols.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise. The invention illustratively disclosed herein suitably may be practiced in the absence of any element or step which is not specifically disclosed herein.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps may be combined, omitted, or further subdivided into additional steps.

All patents, publications, and references cited herein are hereby fully incorporated by reference. In case of conflict between the present disclosure and incorporated patents, publications and references, the present disclosure should control.

What is claimed:

1. A method of fractionating a sample comprising a mixture of a first fraction and a second fraction, comprising:
    contacting a sample comprising a mixture of a first and a second fraction to a polymer brush comprising a substrate and a polymer chain attached to and extending outwardly from the substrate;
    selectively sorbing one of the first and second fractions from the sample with the polymer chain; and,
    releasing the sorbed fraction from the polymer chain by stimulating the polymer chain with a first stimulus to contract the polymer chain.

2. The method of claim 1, further comprising selectively removing the non-sorbed fraction from the polymer brush before releasing the sorbed fraction from the polymer chain.

3. The method of claim 1, further comprising characterizing one or both of the first and second fractions using an analytical method selected from the group consisting of MALDI MS, fluorescence spectroscopy, surface plasmon spectroscopy, and secondary ion mass spectrometry.

4. The method of claim 1, further comprising stimulating the polymer chain with a second stimulus to expand the polymer chain before contacting the sample to the polymer brush.

5. The method of claim 1, wherein the sample provides a second stimulus that causes the polymer chain to expand when contacted with the sample.

6. The method of claim 1, wherein the substrate is formed from a material selected from the group consisting of inorganic metals, silicon oxides, the nuclei of a hyperbranched polymer, high surface area oxides, organic polymer films, sol-gels, carbon nanotube composites, MALDI targets, and combinations thereof.

7. The method of claim 1, wherein the substrate is selected from the group consisting of polystyrenes, polyacrylates, polymethacrylates, polyolefins, polyesters, polyamides, polycarbonates, polysiloxanes, polythiophenes, polyacetylenes, polypyrroles, polyanilines, polyfluorenes, polytetrathiafulvalenes, polynaphthalenes, polyphenylenevinylenes, polysilanes, and combinations thereof.

8. The method of claim 1, wherein the polymer chain is selected from the group consisting of a homopolymer, a random copolymer, an alternating copolymer, a hyperbranched polymer, a dendron, a block copolymer, and combinations thereof.

9. The method of claim 1, wherein the polymer chain comprises one of an anionic polymer chain, a cationic polymer chain, and a neutral polymer chain.

10. The method of claim 9, wherein the target fraction has a complementary charge to the polymer chain.

11. The method of claim 1, wherein the polymer chain comprises a functional group selected from the group consisting of a pH-sensitive functional group, a magnetic functional group, an ionic strength-sensitive group, a temperature-sensitive group, a dipolar functional group, a photo-acid, a photoisomerizable functional group, and combinations thereof.

12. The method of claim 1, wherein the first and/or second polymer chains are attached to the substrate by a process selected from the group consisting of covalent bonding, non-covalent bonding, grafting-to, grafting-from, and combinations thereof.

13. The method of claim 1, wherein the polymer chain comprises a monomer having the structure

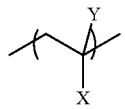

comprising functional groups X and Y.

14. The method of 13, wherein the functional group Y is selected from the group consisting of hydrogen, $(C_1\text{-}C_{20})$ alkyl, $(CH_2OC_nH_{2n+1})$alkoxy, $(C_1\text{-}C_{20})$fluoroalkyl, $(CH_2OC_nF_{2n+1})$fluoroalkoxy, aryl, halogen, nitrile, hydroxyl, and combinations thereof.

15. The method of claim 13, wherein the functional group X is selected from the group consisting of quarternary ammonium salts, N-alkyl pyridines, nitrogen oxides, hydroxyls, carboxylic acids, amines, sulfonic acids, phosphoric acids, spiropyran, oxazine, fulgimide, dihydroindolizine, o-nitrobenzyl ester, alpha-diazoketone, diazonium salt, and combinations thereof.

16. A method of assaying for a target fraction in a sample, comprising:
    contacting a sample to a polymer brush comprising a substrate and a polymer chain attached to an extending from the substrate;
    selectively sorbing a target fraction, if present, with the polymer chain;
    stimulating the polymer chain with a first stimulus to contract the polymer chain and release the sorbed target fraction, if present.

17. The method of claim 16, further comprising characterizing the released target fraction.

18. The method of claim 17, comprising characterizing the released fraction using an analytical method selected from the group consisting of MALDI MS, fluorescence spectroscopy, surface plasmon spectroscopy, and secondary ion mass spectrometry.

19. The method of claim 16, wherein the polymer chain is provided with an anionic or cationic functionality to selectively sorb a cationic or anionic target fraction, respectively.

20. A method of extracting a target fraction from a sample, comprising:
    contacting a sample comprising first and second fractions to a polymer brush array, the polymer brush array comprising first and second polymer brushes and a substrate, the polymer brushes each comprising a polymer chain attached to and extending outwardly from the substrate;
    selectively sorbing the first fraction with the first polymer brush and selectively sorbing the second fraction with the second polymer brush; and selectively stimulating the first polymer brush with a first stimulus to contract the first polymer brush and release the first fraction.

21. The method of claim 20, further comprising removing the released first fraction and selectively stimulating the second polymer brush with a second stimulus, same or different from the first stimulus, to contract and release the second fraction.

22. An array of polymer brushes, comprising a substrate;

a first polymer brush comprising a first polymer chain attached to the substrate; and a second polymer brush comprising a second polymer chain attached to the substrate;

wherein the first polymer chain selectively sorbs a first fraction of a sample and the second polymer chain selectively sorbs a second fraction of the sample, the first polymer chain contracting in response to a first contracting stimulus to release a sorbed first fraction, and the second polymer chain contracting in response to a second contracting stimulus, same or different from the first stimulus, to release a sorbed second fraction.

* * * * *